(12) United States Patent
Kim

(10) Patent No.: US 9,212,221 B2
(45) Date of Patent: Dec. 15, 2015

(54) FORM-SPECIFIC ANTIBODIES FOR NAG-1 (MIC-1, GDF-15), H6D AND OTHER TGF-β SUBFAMILY AND HEART DISEASE AND CANCER DIAGNOSES

(75) Inventor: Hyesook Kim, Bloomfield Hills, MI (US)

(73) Assignee: Detroit R & D, Inc., Detroit, MI (US)

( * ) Notice: Subject to any disclaimer, the term of this patent is extended or adjusted under 35 U.S.C. 154(b) by 415 days.

(21) Appl. No.: 13/039,894

(22) Filed: Mar. 3, 2011

(65) Prior Publication Data

US 2011/0262444 A1    Oct. 27, 2011

Related U.S. Application Data

(60) Provisional application No. 61/309,950, filed on Mar. 3, 2010.

(51) Int. Cl.

| | |
|---|---|
| C07K 1/00 | (2006.01) |
| C07K 16/00 | (2006.01) |
| C07K 16/18 | (2006.01) |
| C07K 16/22 | (2006.01) |
| C07K 16/28 | (2006.01) |
| C07K 16/30 | (2006.01) |
| A61K 6/00 | (2006.01) |
| A61K 47/00 | (2006.01) |
| G01N 33/574 | (2006.01) |

(52) U.S. Cl.
CPC ............... *C07K 16/22* (2013.01); *G01N 33/574* (2013.01); *C07K 2317/33* (2013.01); *C07K 2317/34* (2013.01)

(58) Field of Classification Search
CPC .......... C07K 1/00; C07K 16/00; C07K 16/18; C07K 16/22; C07K 16/28; C07K 16/30; C07K 2299/00; C07K 2317/00; C07K 2317/30; C07K 2317/33; C07K 2317/34; A61K 6/00; A61K 47/00; A61K 47/48; A61K 47/48369; A61K 47/48376; A61K 47/48507; A61K 47/48515; A61K 47/48523; A61K 47/48538; A61K 47/48569; G01N 1/00; G01N 33/00

See application file for complete search history.

(56) References Cited

U.S. PATENT DOCUMENTS 6,846,634 B1 * 1/2005 Tomlinson et al. ............... 506/9

FOREIGN PATENT DOCUMENTS

WO       WO-0181928       * 11/2001

OTHER PUBLICATIONS

Martinez, et al., Drug-Induced Expression of Nonsteroidal Anti-Inflammatory Drug-Activated Gene/Macrophage Inhibitory Cytokine-1/Prostate-Derived Factor, a Putative Tumor Suppresssor, Inhibits Tumor Growth, The Jornal of Pharmacology and Experimental Therapeutics, vol. 318, No. 2, 2006, pp. 899-906.
Baek, et al., Cyclooxygenase Inhibitors Regulate the Expression of a TGF-Beta Superfamily Member That Has Proapoptotic and Antitumorigenic Activities, Molecular Pharmacology, vol. 59, No. 4, 2001, pp. 901-908.
Eling, et al., NSAID Activated Gene (NAG-1), a Modulator of Tumorigenesis, Journal of Biochemistry and Molecular Biology, vol. 39, No. 6, 2006, pp. 649-655.
Brown, et al., Antibody-Based Approach to High-Volume Genotyping for MIC-1 Polymorphism, Biotechniques, vol. 33, No. 1, 2002, pp. 118-120.
Welsh, et al., Large-scale delineation of secreted protein biomarkers overexpressed in cancer tissue and serum, PNAS, vol. 100, No. 6, 2003, pp. 3410-3415.
Selander, et al., Serum Macrophage Inhibitory Cytokine-1 Concentrations Correlate with the Presence of Prostate Cancer Bone Metastases, Cancer Epidemiol Biomarkers Prev 16, 2007, pp. 532-537.
Brown, et al., Measurement of Serum Levels of Macrophage Inhibitory Cytokine 1 Combined with Prostate-Specific Antigen Improves Prostate Cancer Diagnosis, Clin Cancer Res 12, 2006, pp. 89-96.
Fairlie, et al., MIC-1 is a novel TGF-Beta superfamily cytokine associated with macrophage activation, Jornal of Leukocyte Biology, vol. 65, 1999, pp. 2-5.
Lindmark, et al., H6D Polymorphism in Macrophage-Inhibitory Cytokine-1 Gene Associated With Prostate Cancer, Journal National Cancer Institute, vol. 96, 2004, pp. 1248-1254.
Hayes, et al., Macrophage Inhibitory Cytokine-1 H6D Polymorphism, Prostate Cancer Risk, and Survival, Cancer Epidemiol Biomarkers Prev 15, 2006, pp. 1223-1225.
Fairlie, et al., Epitope Mapping of the Transforming Growth Factor-Beta Superfamily Protein, Macrophage Inhibitory Cytokine-1 (MIC-1): Identification of at Least Five Distinct Epitope Specificities, Biochemistry 40, 2001, pp. 65-73.
Yamaguchi, et al., Molecular characterisation of canine nonsteroidal anti-inflammatory drug-activated gene (nag-1), The Veterinary Journal 175, 2008, pp. 89-95.
Hutson, et al., Protein Engineering of Single-Chain Fv Analogs and Fusion Proteins, Methods in Enzymology, , vol. 203, 1991, pp. 46-88.
Johnson, et al., Construction of Single-Chain Fv Derivatives of Monoclonal Antibodies and Their Production in *Escherichia coli*, Academic Press, Inc., 1991, pp. 88-89.

(Continued)

Primary Examiner — Alana Harris Dent

(74) Attorney, Agent, or Firm — Kohn & Associates, PLLC

(57) ABSTRACT

A method of producing form-specific anti-peptide antibodies for a wild type protein and its one amino acid mutated protein using a peptide antigen, by obtaining a protein sequence of the wild type protein and its one amino acid mutated protein, selecting a continuous amino acid sequence without any internal cysteine residues that includes the one amino acid mutated sequence and wild type sequence corresponding to the mutated site at the end of the sequence to obtain a synthetic mutation peptide and a synthetic wild type peptide, conjugating the synthetic peptides to a carrier protein, and immunizing an animal to produce antibodies. Methods of detecting cancer and methods of treating cancer.

6 Claims, 6 Drawing Sheets

(56) References Cited

OTHER PUBLICATIONS

Mernaugh, et al., An Overview of Phage-Displayed Recombinant Antibodies, Molecular Methods in Plant Pathology (RP Singh and U.S. Singh, eds.; CRC Press Inc., Boca Raton, FL), pp. 359-365, 1995.

Johnen, et al., Tumor-induced anorexia and weight loss are mediated by the TGF-Beta superfamily cytokine MIC-1, Nature Medicine, vol. 13, No. 11, 2007, pp. 1333-1340.

Neslund-Dudas, et al., SRD5A2 and HSD3B2 Polymorphisms are Associated With Prostate Cancer Risk and Aggressiveness, National Insitutes of Health, Prostate 67, 2007, pp. 1654-1663.

* cited by examiner

Fig. 1. A-B
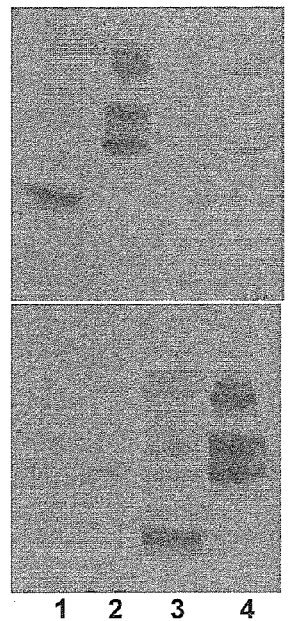
Anti-Peptide 1
Anti-peptide 2
1  2  3  4
Fig. 2. A-B
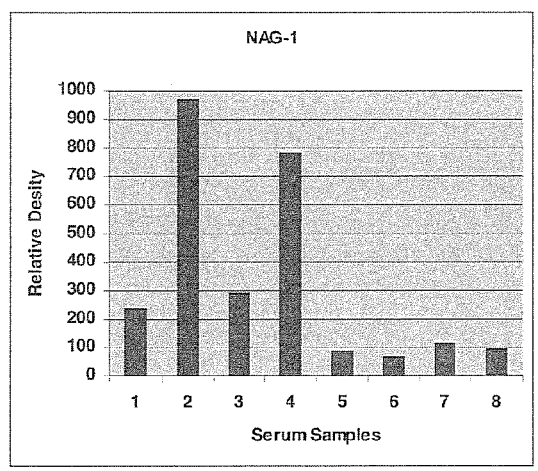
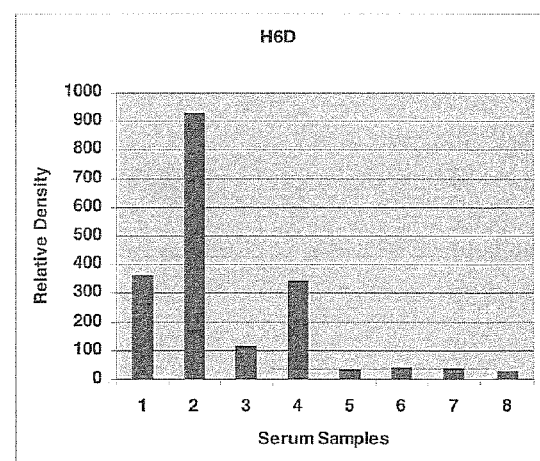

Fig. 4. A-B.
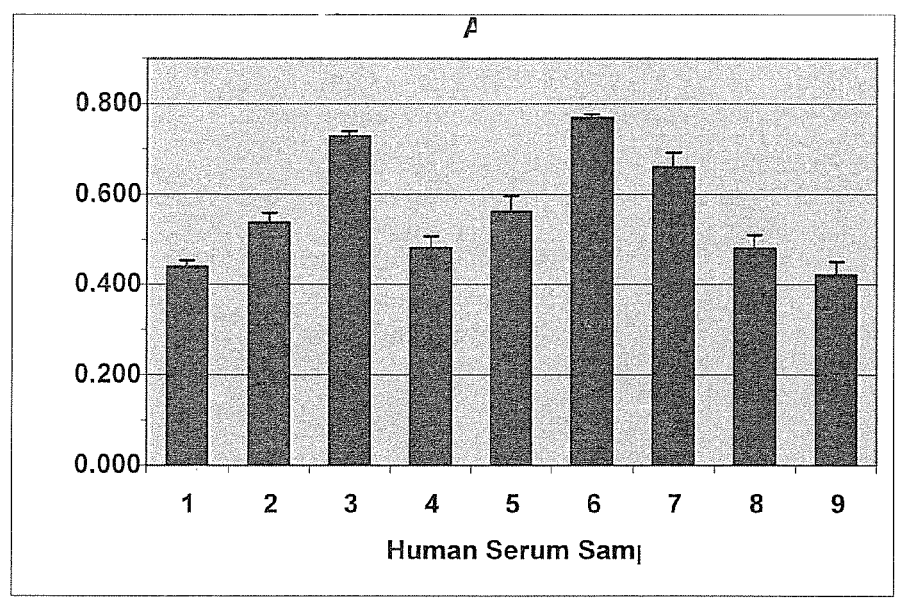
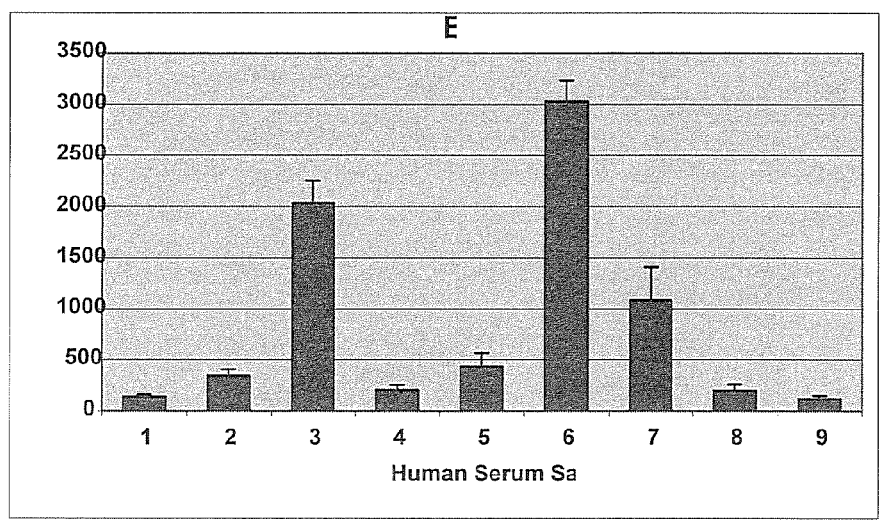
Fig. 5.
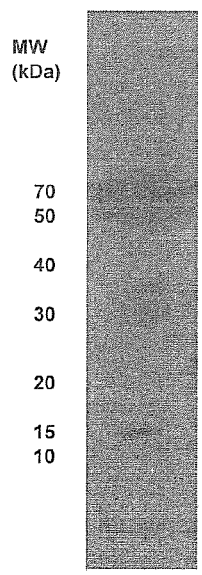

```
                              Cys1  Cys2,3
hH6D  170 laesssarpqlelhlrpqaargrrrararngddcplgpgrCCrlhtvrasledlgwadwv 229  (Seq Id No.: 6)
hWT   170 laesssarpqlelhlrpqaargrrrararngdhcplgpgrCCrlhtvrasledlgwadwv 229  (Seq Id No.: 7)
c     155 laesssrarpqlelhlrsraarglrraarngdhcplgpgrCCrlhtvrasledlgwsdwv 213  (Seq Id No.: 8)
m     168 -lp--sggaqlelrlrvaagrgrrsahahprdscplgpgrCChletvqatledlgwsdwv 224  (Seq Id No.: 9)
r     168 -lp--sggarlelhlrsaagrgrrsahlhprdscplgpgrCChletvqatledlgwsdwv 224  (Seq Id No.: 10)
d     170 alp--sarpqlelhwrpraargrrnahahardgcplgegrCCrlqslraslqdlgwanwv 227  (Seq Id No.: 11)
```

B

Human
```
NAG-1  -16 elhlrpqaargrrrararngdhcplgpgr-CCrlhtvrasledlgwadwvlsprevqvtm  (Seq Id No.: 12)
tgfb1  -16 tpleraqhlqssrhrraldtnycfssteknCCvrqlyidfrkdlgwk-wihepkgyhanf  (Seq Id No.: 13)
tgfb2  -16 psyrlesqqtnrrkkraldaaycfrnvqdnCClrplyidfkrdlgwk-wihepkgynanf  (Seq Id No.: 14)
tgfb3  -16 phrldnpgqggqrkkraldtnycfrnleenCCvrplyidfrqdlgwk-wvhepkgyyanf  (Seq Id NO.: 15)
```

Xenopus
```
tgfb1  -16 mpaeridtvtssrkkrgvgqeycfgnngpnCCvkplyinfrkdlgwk-wihepkgyeanyc (Seq Id No.: 16)
```

C
```
hH6D  170 laesssarpqlelhlrpqaargrrrararngddcplgpgrCCrlhtvrasledlgwadwv 229 (Seq Id No.: 6)
hWT   170 laesssarpqlelhlrpqaargrrrararngdhcplgpgrCCrlhtvrasledlgwadwv 229 (Seq Id No.: 7)
c     155 laesssrarpqlelhlrsraarglrraarngdhcplgpgrCCrlhtvrasledlgwsdwv 213 (Seq Id No.: 8)
m     168 -lp--sggaqlelrlrvaagrgrrsahahprdscplgpgrCChletvqatledlgwsdwv 224 (Seq Id No.: 9)
r     168 -lp--sggarlelhlrsaagrgrrsahlhprdscplgpgrCChletvqatledlgwsdwv 224 (Seq Id No.: 10)
d     170 alp--sarpqlelhwrpraargrrnahahardgcplgegrCCrlqslraslqdlgwanwv 227 (Seq Id No.: 11)
```

D

Human
```
NAG-1  -16 elhlrpqaargrrrararngdhcplgpgr-CCrlhtvrasledlgwadwvlsprevqvtm  (Seq Id No.: 12)
tgfb1  -16 tpleraqhlqssrhrraldtnycfssteknCCvrqlyidfrkdlgwk-wihepkgyhanf  (Seq Id No.: 13)
tgfb2  -16 psyrlesqqtnrrkkraldaaycfrnvqdnCClrplyidfkrdlgwk-wihepkgynanf  (Seq Id No.: 14)
tgfb3  -16 phrldnpgqggqrkkraldtnycfrnleenCCvrplyidfrqdlgwk-wvhepkgyyanf  (Seq Id No.: 15)
```

Xenopus
```
tgfb1  -16 mpaeridtvtssrkkrgvgqeycfgnngpnCCvkplyinfrkdlgwk-wihepkgyeanyc (Seq Id No.: 16)
```

Fig. 7. A-B
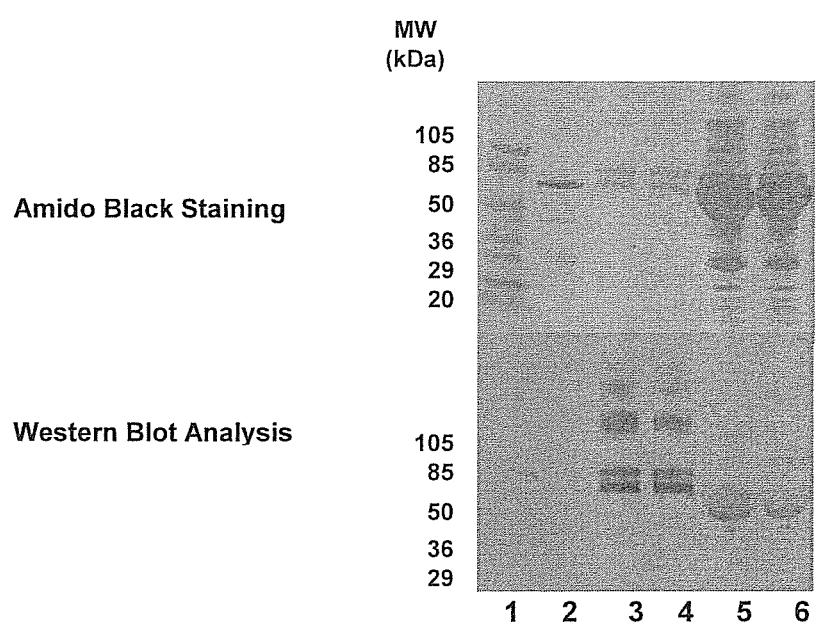

Fig. 8. A-B.
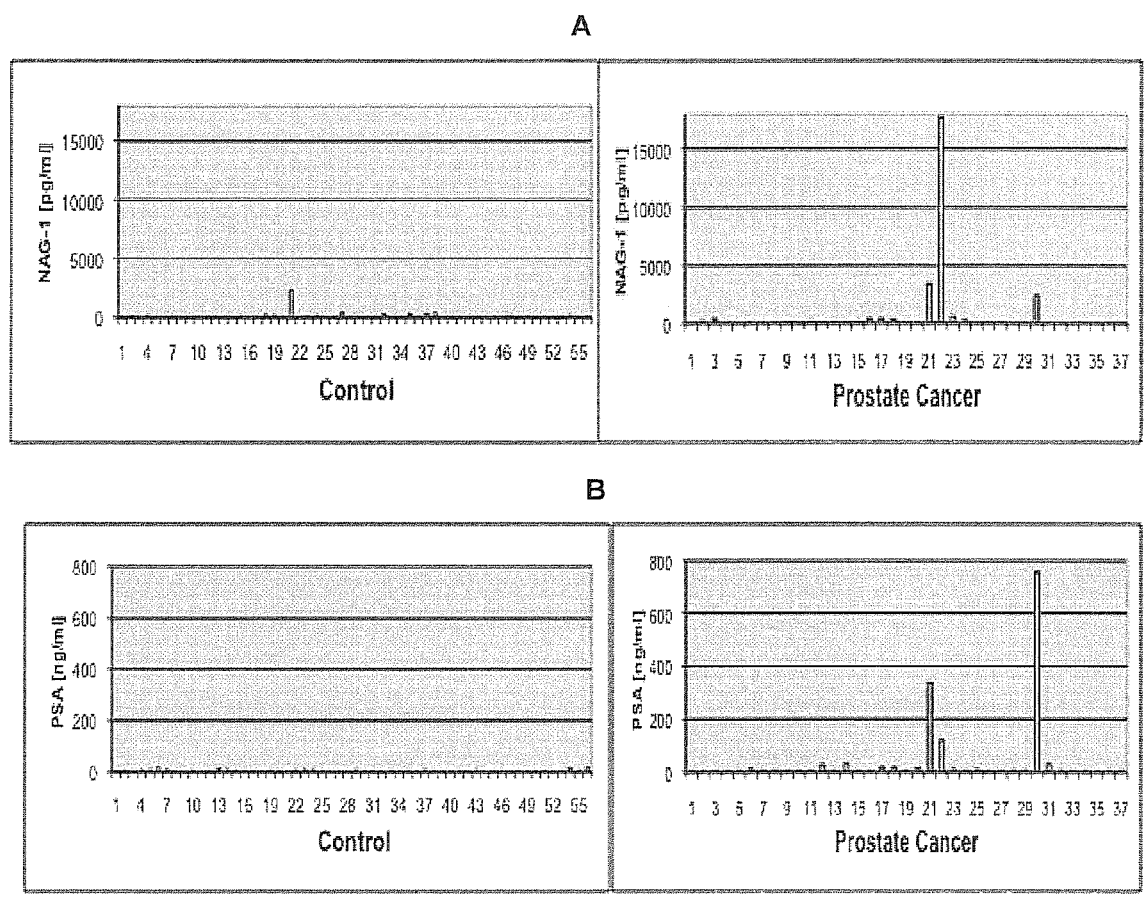

FORM-SPECIFIC ANTIBODIES FOR NAG-1 (MIC-1, GDF-15), H6D AND OTHER TGF-β SUBFAMILY AND HEART DISEASE AND CANCER DIAGNOSES

GRANT INFORMATION

Research in this application was supported in part by contracts from the National Institute of Environmental Health Sciences (NIEHS Contracts HHSN273200700012C and HHSN2732000800006C).

BACKGROUND OF THE INVENTION

1. Technical Field

The present invention relates to methods of producing form-specific antibodies for transforming growth factor (TGF)-β subfamily compositions. More specifically, the present invention relates to methods of diagnosing cancer patients by measuring levels using antibodies.

2. Background Art

Nonsteroidal anti-inflammatory drug-activated gene (NAG-1)/macrophage inhibitory cytokine (MIC-1)/prostate-derived factor (PDF)-15/growth differentiation factor 15 (GDF)-15 is a member of TGF-β subfamily that plays an important role in pro-apoptotic and anti-tumoric activities as well as anti-inflammatory response to infection (1,2). High NAG-1 protein expression has been observed in tumors (3) and cardiovascular diseases (4) and became a therapeutic target.

Cleaved, matured NAG-1 expression increased in the serum of patients with the progression of the prostate cancer metastasis including bone metastasis (5,6). However, in a 2006 study with 462 control and 538 prostate cancer patients, it has been reported that serum NAG-1 levels were lower in the prostate cancer group compared with benign disease (BPH) and control (7).

The human NAG-1 protein is synthesized as a 308-amino acid pro-peptide, cleaved by a protease to a mature 112-amino acid protein and secreted as a disulfide-linked homodimer (8). A single-nucleotide polymorphism (SNP) at position 6 of the mature protein (code 604, CAC to GAC) results in a substitution of histidine to aspartic acid (H6D), which has a potential to alter the function of the protein (9). Indeed, a genotyping and sequencing analysis of genomic DNA for 1383 cases of prostate cancer and 789 control subjects in Sweden demonstrated that the H6D polymorphism in NAG-1/MIC-1 gene is associated with sporadic and familial cases of prostate cancer (9). A genotyping of genomic DNA for 819 cases of prostate cancer and 731 control subjects in Australia found that HD or DD genotype had increased risk of death from prostate cancer compared with HH genotype (10).

Compared to the DNA genotyping, serum genotyping is more convenient and faster because blood sampling is a routine at clinics and the ELISA result is obtained in 2-4 hours but requires antibodies specific for each wild type and mutated protein. Previously, a Mab-based genotyping assay has been developed to analyze the major allelic forms of NAG-1/MIC-1 on the basis of one of their monoclonal antibodies (13C4H4) which had a markedly reduced affinity for the MIC-1 D protein (4,11), because a H6D-specific antibody is not available. The genotype of a serum sample was determined by ratio of the 13C4H4 assay level to the level of total NAG-1 detected by 26G6H6 assay. The HH (homozygous H), HD (heterozygous) and DD (homozygous D) genotypes were determined by ratio ranges of 0.6-1.4, 0-0.45 and <0, respectively. The ranges of ratios, 0.6-1.4, 0-0.45 and <0, respectively, were randomly decided. Otherwise, it had to be 1, 0.5 and 0, respectively, or 0.75-1.25, 0.25-0.75 and 0-0.25, respectively. By looking at the ratios to predict the genotype, this method would not work because a negative ration would be needed to obtain a homozygous D genotype. The ELISA result obtained with a plate coated with the 13C4H4 monoclonal antibodies produced by immunization of His-containing wide type NAG-1 was inversely related with H6D protein concentration. Addition of 20 pg/ml and 70 pg/ml H6D proteins in the ELISA produced an optical density (OD) 20% and 30%, respectively, lower than the background OD (4,11).

Therefore, there remains a need to produce form-specific antibodies for wild type NAG-1 and HD6 that distinguish His from Asp at the $6^{th}$ position of the proteins.

SUMMARY OF THE INVENTION

The present invention provides for a method of producing form-specific anti-peptide antibodies for a wild type protein and its one amino acid mutated protein using a peptide antigen, by obtaining a protein sequence of the wild type protein and its one amino acid mutation protein, selecting a continuous amino acid sequence without any internal cysteine residues that includes the one amino acid mutated sequence and wild type sequence corresponding to the mutated site at the end of the sequence to obtain a synthetic mutation peptide and a synthetic wild type peptide, conjugating the synthetic peptides to a carrier protein, and immunizing an animal to produce antibodies.

The present invention also provides for a method of detecting cancer, by measuring an amount a wild type epitope and its one amino acid mutated epitope in a biological system, comparing the amounts to a control sample, and if the amount of wild type epitopes and one amino acid mutated epitopes are higher than amount of the control sample, detecting the presence of cancer.

The present invention provides for a method of treating cancer, by administering an effective amount of anti-peptide form-specific antibodies that react with wild type NAG-1 and an H6D polymorphism.

The present invention further provides for a method of detecting the presence of cancer, by measuring an amount of PSA or an amount of NAG-1 in a biological system, and if the amount of PSA or NAG-1 is higher than control samples, detecting the presence of inflammation and cancer.

DESCRIPTION OF THE DRAWINGS

Other advantages of the present invention are readily appreciated as the same becomes better understood by reference to the following detailed description when considered in connection with the accompanying drawings wherein:

FIGS. 1A-1B are graphs showing Western blot analyses with rabbit polyclonal antibodies for Peptide 1 (CRNGDH, SEQ ID NO: 1) and Peptide 2 (CRNGDD, SEQ ID NO: 2) conjugated to BSA and OVA (Lane 1, OVA-peptide 1, lane 2, BSA-peptide 1, lane 3, OVA-peptide 2 and lane 4, BSA-peptide 2, each lane was loaded with 2 μg of protein);

FIGS. 2A-2B are graphs showing decreased NAG-1 and H6D levels in serum samples obtained from lung cancer patients, cleaved 40 kDa NAG-1 (wild type) and H6D band intensities were obtained after Western blot analysis under non-reducing conditions using NAG-1- and H6D-specific antibodies, respectively;

FIGS. 4A-4B are graphs showing NAG-1 sandwich ELISA analyses of immunoreactive proteins expressed in human COPD patient serum samples (25 μl/well) using antibodies produced with the NAG-1 peptide (RNGDH, SEQ ID NO: 3), Panel A, optical density at 450 nm and Panel B, quantitation using the NAG-1 standard curve shown in FIG. 2, a mean value and standard deviation obtained from triplicate data points are shown;

FIG. 5 is a graph showing Western blot analysis of mouse NAG-1 proteins expressed in mouse serum using mouse anti-peptide antibodies produced against HPRDS (SEQ ID NO: 4) corresponding to RNGDH (SEQ ID NO: 3) or RNGDD (SEQ ID NO: 5), a human NAG-1 sequence;

FIGS. 6A-6D are graphs showing alignment of partial NAG-1 protein sequences with NAG-1 sequences of other species (Panels A and C (SEQ ID NOS: 6-11)) and TGF-beta subfamily proteins (Panels B and D (SEQ ID NOS: 12-16)); Panels A and B, sequences selected for anti-peptide antibodies for both cleaved and pro-proteins and Panels C and D, sequences selected for N-terminal anti-peptide antibodies primarily for cleaved proteins; the selected sequences are underlined and in bold type; recognition sequences for furin digestion (RXXR) (SEQ ID NO: 30) are in bold type; the tertiary structure of the TGF-beta subfamily is highly conserved among various subfamily and species; the first 3 Cys residues involved with intra or inter disulfide bonding are shown in bold type; Panels A and C, full sequence alignment published by Yamaguchi et al. (12) with human H6D sequence (hH6D) is modified to add human wild type (hWT) NAG-1 sequence; c, chimpanzee, m, mouse, r, rat and d, dog; Panels B and D, alignment of partial human NAG-1 protein sequence with various TGF-beta subfamily sequences; Ala or Gly of the first amino acid residue of the cleaved NAG-1 or other TGF-beta subfamily is designated as No. 1;

FIGS. 7A-7B are graphs showing Western blot analyses of anti-serum produced by immunization of rabbits with KLH-conjugated Peptide 1 (ARNGDHC) (SEQ ID NO: 28). Lanes 1, pre-stained molecular weight standards, lane 2, BSA, lane 3, BSA conjugated with Peptide 1 (NAG-1), lane 4, BSA conjugated with Peptide 2 (H6D) and lanes 5 and 6, human plasma samples; and FIGS. 8A-8B are graphs showing comparison of NAG-1 levels with PSA levels of control and prostate cancer plasma samples shown in Table 3.

DETAILED DESCRIPTION OF THE INVENTION

Figure 3:
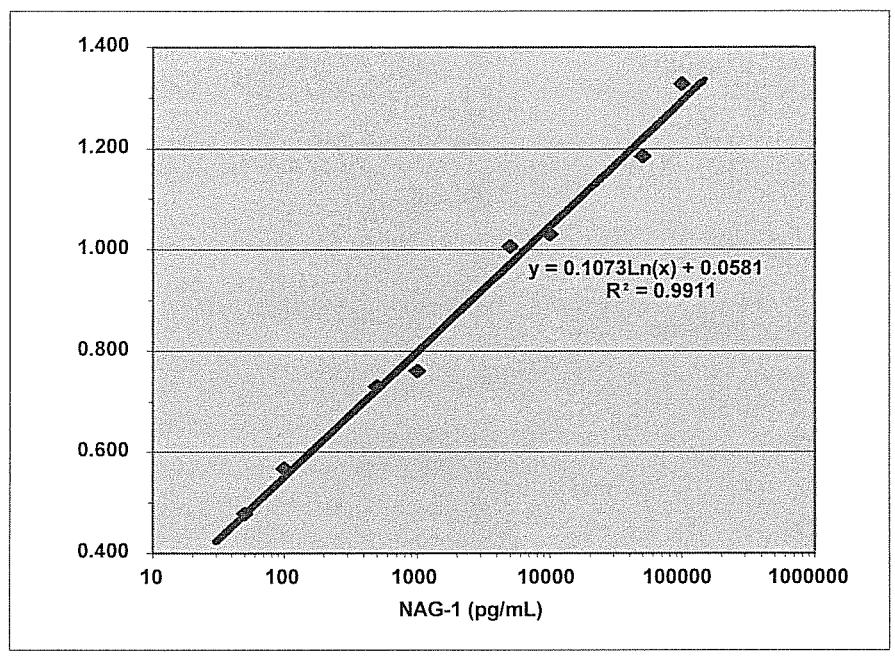
FIG. 3 is a graph showing wild type NAG-1 sandwich ELISA produced with anti-NAG-1 produced for N-terminal sequence of cleaved NAG-1 (RNGDH, SEQ ID NO: 3) at Detroit R&D with monoclonal detection antibodies.

The present invention is generally directed to antigen peptides that produce antibodies, which distinguish the wild type NAG-1 sequence from mutation (FIGS. 1-3, Table 1 and 2).

NAG-1, also referred to as MIC-1 or GDF-15, belongs to TGF-beta subfamily, highly conserved in tertiary structures of the mature cleaved protein sequences, especially in the 8 Cys residues for intra and inter disulfide bondings, which produce similar molecular structures among TGF-beta subfamily. In addition, the molecular structure of the subfamily is highly conserved among various species (FIG. 6). The human NAG-1 antigen sequences, RNGDH (SEQ ID NO: 3) and RNGDD (SEQ ID NO: 5) were aligned with mouse NAG-1 sequence using the first 3 Cys residues conserved among various species, an antigen peptide for mouse was identified, HPRDS (SEQ ID NO: 4), and mouse NAG-1 anti-peptide antibodies were produced after conjugation of the peptide to KLH via N-terminal Cys added to the sequence as was carried out with human NAG-1 sequences, RNGDH (SEQ ID NO: 3) and RNGDD (SEQ ID NO: 5). Considering only 1 out of 5 amino acid residues conserved between the mouse and human sequences, it is a surprise to find an epitope favorable for the mouse NAG-1 antibody production.

A DNA genotyping study of NAG-1 found that the H6D polymorphism was associated with lower risk of developing prostate cancer but with prostate cancer metastasis and increased risk of death from the cancer (10). Prostate cancer development can be prevented by treatment of an antibody specific for HH wild type NAG-1 and prevention of metastasis and death from cancer by treatment of H6D antibodies.

mRNA and protein expressions and processing of TGF-beta subfamily proteins to a biologically active mature form are extensively regulated. The H6D polymorphism-induced alteration of various biological events has not been actively studied due to lack of antibodies that can distinguish the wild type NAG-1 protein from the H6D polymorphism. The present invention solves this problem.

Generally, the present invention provides for a method of producing form-specific anti-peptide antibodies for a wild type protein and its one amino acid mutation protein using a peptide antigen by obtaining a protein sequence of the wild type protein and its one amino acid mutation protein, selecting a continuous amino acid sequence without any internal cysteine residues which includes the one amino acid mutation sequence and wild type sequence corresponding to the mutated site at the end of the sequence to obtain a synthetic mutation peptide and a synthetic wild type peptide, conjugating the synthetic peptides to a carrier protein, and immunizing an animal to produce antibodies.

The synthetic mutation peptide can be conjugated to a carrier protein via an amino acid at the opposite end of an end having the mutated amino acid sequence. Also, the synthetic mutation peptide and the synthetic wild type peptide can be conjugated to the carrier molecule via a cysteine residue.

The synthetic mutation peptide and synthetic wild type peptide are preferably 4-mer-10-mer. The protein sequence is preferably a member of the transforming growth factor (TGF)-beta subfamily. More preferably, the wild type protein is NAG-1 and the one amino acid mutation protein is an H6D polymorphism, and the antibodies produced are form-specific to NAG-1 and the H6D polymorphism.

An antigen peptide sequence with 5-9 residues or extended to the next downstream residue of SEQ ID NO: 30 can be selected, which C-terminally ends with an amino acid sequence corresponding to the peptide sequence, SEQ ID NO: 3 and SEQ ID NO: 5 of wild type NAG-1 and H6D proteins. An amino acid sequence can be selected corresponding to the peptide sequence SEQ ID NO: 3 and SEQ ID NO: 5. In this case, the peptides can be conjugated to carrier proteins via N-terminal amino acid including N-terminal Cys added to the peptide. Also an amino acid sequence corresponding to the peptide sequence SEQ ID NO: 28 and SEQ ID NO: 29 can be selected. Other amino acid sequences can be selected as further described herein.

The protein sequence can be for an animal other than human, and the selecting step then further includes the step of aligning the animal protein sequence with the human protein sequence.

This method can also include the step of purifying the antibodies by eliminating any antibodies that cross-react with Arg-containing N-terminal peptides of cleaved proteins. The presence of antibodies can be confirmed by taking a sample from the patient and performing an assay such as, but not limited to, ELISA, radioimmunoassay, or fluoroimmunoassay.

The proper peptides were designed for raising specific antibodies to wild type NAG-1 and its polymorphism H6D. Because there is only one amino acid difference between the NAG-1 and H6D, it was a challenge to make two antibodies, which distinguish the wild type from the mutant. Form-specific antibodies cannot be produced with the target amino acid in the middle of an antigen peptide. Moreover, Cys next to H6 or D6, poses a problem. To overcome this challenge, N-terminal peptides were made such as Anti-Peptide 1 cross-reacted with BSA- or OVA-Peptide 1 but NOT with BSA- or OVA-Peptide 2 and anti-Peptide 2 cross-reacted with BSA- or OVA-Peptide 2 but NOT with BSA- or OVA-Peptide 1 (FIGS. 1A-1B). For the NAG-1 and CRNGDD (SEQ ID NO: 2) for the H6D where Cys replaced the N-terminal Ala and the N-terminal Cys was conjugated with KLH (see Example 1). Thus, the H6 or D6 was protruded to solution.

CRNGDH (Peptide 1, SEQ ID NO: 1) and CRNGDD (Peptide 2, SEQ ID NO: 2) peptides were conjugated with KLH for rabbit polyclonal antibodies for wild type NAG-1 and H6D proteins, respectively. High titers of the antibodies were obtained by conventional (direct) ELISA using a plate coated with peptide-conjugated BSA and free BSA (negative control) (see Example 2). Specificity of the wild type NAG-1 and H6D antibodies was tested using peptide-conjugated with BSA or OVA by Western blot analyses.

As shown in FIGS. 1A-1B, antibodies produced using Peptide 1 (CRNGDH (SEQ ID NO: 1)) and Peptide 2 (CRNGDD (SEQ ID NO: 2)) conjugated to KLH with high titers detected by ELISA were extremely form-specific. No non-specific cross-reactivity was detected with both antibodies. Considering that only one amino acid difference between the two antigen peptides, the specificity of the antibodies was surprising. Whereas addition of the Peptide 1 (CRNGDH (SEQ ID NO: 1)) minimally inhibited, addition of the Peptide 2 (CRNGDD (SEQ ID NO: 2)) substantially (81%) inhibited cross-reactivity of the H6D antibodies with the Peptide 2 (CRNGDD (SEQ ID NO: 2))-conjugated BSA in Western blot analysis. This result further proved specificity of the antibodies.

Hybridomas were obtained after immunization of mice with the Peptide 1 (CRNGDH (SEQ ID NO: 1)) conjugated to KLH. ELISA carried out with a plate coated with Peptide 1- and Peptide 2-conjugated OVA revealed that supernatants obtained from 3 hybridomas recognized primarily the Peptide-1-OVA conjugates. Supernatant of a hybridoma obtained with the Peptide 2 (CRNGDD) conjugates recognized primarily the Peptide-2-OVA conjugates in the ELISA (see Tables 1 and 2). This result further confirms specificity of the antibodies produced with the antigen peptides, Peptide 1 (CRNGDH (SEQ ID NO: 1)) and Peptide 2 (CRNGDD (SEQ ID NO: 2)), conjugated to KLH via N-terminal Cys.

The successful form-specific NAG-1 and H6D polyclonal antibody production proved that the method was correct, which was the first report that showed production of form-specific antibodies for wild type NAG-1 and H6D protein. These results demonstrated that antibodies, which distinguish a wild type protein from one amino acid mutated protein, can be produced using an antigen peptide as described above.

Feasibility of use of NAG-1 and H6D antibodies for human serum/plasma screening was demonstrated by Western blot analyses with serum samples obtained from 9 patients with chronic obstructive pulmonary disease (COPD) and 4 controls and 4 lung cancer patients (see Example 4). Differential expression levels of ~40 kDa and total immunoreactive H6D or NAG-1 proteins in the human sera were detected, i.e., one of the COPD patient sera contained ~4-fold higher level of the 40 kDa wild type NAG-1 species compared with H6D and one of the control sera showed the level of wild type NAG-1 much higher than the H6D level (FIG. 2, Serum #4).

A sandwich ELISA for quantification of the wild type NAG-1 in the range of 50 pg/ml-500 ng/ml was developed. Sensitivity of the ELISA was <50 pg/ml and $R^2$ value of the graph was >0.99 (see Example 5, FIG. 3). Range of the wild type NAG-1 levels in human serum samples obtained from 9 COPD patients were ~100 pg/ml-3 ng/ml (see Example 6, FIG. 4). The wild type NAG-1 levels obtained from 2 COPD patient serum samples were higher than the previously reported normal serum NAG-1 levels 240-1478 pg/ml) (19). This result strongly demonstrated that the NAG-1 ELISA is useful to distinguish serum NAG-1 levels higher than the normal range most likely due to pulmonary inflammation of the patients.

Monoclonal antibodies, which were thought to bind wild type NAG-1 proteins better than H6D, have been produced by immunization mice with wild type NAG-1 proteins but they were not useful for form-specific Western blot analysis or ELISA. Methodologies were successfully developed for production of polyclonal and monoclonal antibodies to screen NAG-1 and H6D polymorphism by Western blot analysis and ELISA. It was a surprise that immunization of a rabbit with short antigen peptides ending with H or D to protrude toward solution during antibody production resulted in quality antibodies that distinguished one amino acid difference and form-specific when they were used in Western blot analysis, which was under denaturing condition. To be useful for ELISA analysis, the antibodies had to detect epitopes located on the surface of the native wild type and H6D proteins. The result obtained with ELISA demonstrated that epitopes of the wild type NAG-1 and H6D NAG-1 were located on the surface of the proteins.

A method to produce form-specific antibodies for NAG-1, H6D polymorphism or other members of the transforming growth factor (TGF)-beta subfamily in human and other species is also disclosed. The method includes cleavage-specific antibody production for NAG-1, H6D polymorphism or other members of the transforming growth factor (TGF)-beta subfamily in human and other species.

Previous studies found that primarily cleaved, mature TGF-beta subfamily proteins including NAG-1 proteins were detected in blood. The mature proteins of ~110-150 amino acid residues have 8-9 Cys residues which produce a tight structured molecule containing 3-4 intra disulfide bonds and a inter disulfide bond for dimer formation. All 9 Cys are conserved among NAG-1 proteins in various species (FIG. 6, Panels A and C (SEQ ID NOS: 6-11)) and majority of TGF-beta subfamily (FIG. 6, Panels B and D (SEQ ID NOS: 12-16)). The first Cys is missing in other member of TGF-beta superfamily. However, existence of Cys-Cys ($2^{nd}$ and $3^{rd}$ out of 9 Cys) 9 residues downstream of the first Cys site makes the alignment accurate.

The methodology of producing anti-peptide antibodies for other species was tested against the sequence corresponding to the human NAG-1 sequences used for form-specific antibody production, Peptide 1 (RNGDH (SEQ ID NO: 3)) and Peptide 2 (RNGDD (SEQ ID NO: 5)). The sequence alignments with NAG-1 sequences of chimpanzee, mouse rat and dog were carried out as previously reported by Yamaguchi et al. (12) with modification (FIG. 6, A and C). A peptide sequence, HPRDS (SEQ ID NO: 4), was selected for mouse-specific anti-peptide antibody production though only 1 amino acid out of 5 was conserved and anti-mouse NAG-1 polyclonal antibodies with CHPRDS (SEQ ID NO: 17) conjugated via the N-terminal Cys were successfully produced as evidenced by Western blot analysis shown in Example 7, FIG.

5. This result demonstrated that the sequence alignment for antigen peptide selection could accurately predict outcome of the antibody production. Considering highly conserved tertiary structure among the TGF-beta subfamily, the mouse NAG-1 antibodies are most likely suitable for ELISA.

The length of antigen peptides for species other than human and chimpanzee can be N-terminally extended to the end of the cleaved NAG-1 without compromising antibody quality because the sequences still end with the amino acid sequence corresponding to human RNGDH (SEQ ID NO: 3) which protrude toward solution during antibody production. For example, the mouse and rat NAG-1 antigen peptide sequence can be CSAHAHPRDS (SEQ ID NO: 18), CAHAHPRDS (SEQ ID NO: 19), CHAHPRDS (SEQ ID NO: 20) or CAHPRDS (SEQ ID NO: 21) and dog NAG-1 antigen peptide sequence can be CNAHAHARDG (SEQ ID NO: 22), CAHAHARDG (SEQ ID NO: 23), CHAHARDG (SEQ ID NO: 24) or CAHARDG (SEQ ID NO: 25). For the dog NAG-1, RAAR (SEQ ID NO: 26) at the N-terminus of the GRRNAHAHARDG (SEQ ID NO: 27) is a candidate for an alternative furin cleavage site.

Cleavage-specific antibodies were also produced using ARNGDHC (SEQ ID NO: 28) conjugated to KLH via C-terminal Cys exposing the $NH_3^+$ group of the peptide toward solution during antibody production. The polyclonal antibodies recognized both ARNGDHC (Peptide 1, SEQ ID NO: 28)- and ARNGDDC (Peptide 2, SEQ ID NO: 29)-conjugated BSA in Western blot analyses (FIGS. 7A-7B) because His or Asp located next to the Cys was too close to the KLH for proper antibody production.

This strategy can be used for cleavage-specific antibody production for NAG-1 proteins expressed in other species and in other members of the transforming growth factor (TGF)-beta subfamily after selecting a sequence corresponding to the human peptide sequence, ARNGDHC (SEQ ID NO: 28), as shown in FIG. 6, Panels B and D. Furin cleavage sites, C-terminal of RXXR (SEQ ID NO: 30), for each species and subfamily were marked in bold type in FIG. 6, Panel C and D. In some cases, the sequence has to be extended to the amino acid located at the C-terminus of RXXR (SEQ ID NO: 30). Six amino acids can be selected and Cys is added to the C-terminus of the peptide for conjugation of the peptide to KLH. Addition of Arg to the N-terminus of the selected sequences will produce antigen sequences for pro-NAG-1. The Arg-containing sequences can also be used for further purification of the cleavage-specific antibodies.

The present invention also provides for a method of detecting cancer, by measuring an amount a wild type epitope and its one amino acid mutation epitope in a biological system, comparing the amounts to a control sample, and if the amount of wild type epitopes and one amino acid mutation epitopes are higher than amount of the control sample, detecting the presence of cancer.

Preferably, the wild type epitope is from NAG-1 and the one amino acid mutation epitope is from an H6D polymorphism. However, any other wild type and one amino acid mutated epitope can be used. Also, more preferably, the wild type epitope is SEQ ID NO: 3 and the one amino acid mutation epitope is SEQ ID NO: 5. The wild type epitope can also be SEQ ID NO: 28 and the one amino acid mutated epitope is SEQ ID NO: 29. Preferably, the control sample is from a population that does not have cancer.

The amount of the wild type epitope and its one amino acid mutation epitope can be measured by performing an assay such as, but not limited to, ELISA, radioimmunoassay, or fluoroimmunoassays. The biological system sampled is preferably one of plasma, urine, cerebrospinal fluids, bile and joint fluids.

The cancer detected can be any that are characterized by increased levels of a wild type epitope and its one amino acid mutation epitope. Preferably, the cancer is prostate, breast, colon, or pancreatic. More specifically, cancer-induced inflammation is detected by increased levels of a wild type epitope and its one amino acid mutation epitope.

The present invention also provides for a method of detecting the presence of cancer, by measuring an amount of PSA or an amount of NAG-1 in a biological system, and if the amount of PSA or NAG-1 is higher than control samples, detecting the presence of inflammation and cancer.

Preferably, the amount of PSA or NAG-1 is 10-fold higher than the control samples. Preferably, the PSA amount is higher than 120 ng/ml. Preferably, the NAG-1 amount is higher than 2.4 ng/ml. Preferably, the control sample is from a population that does not have cancer or elevated PSA levels. Both PSA and NAG-1 can also be measured in this method, and not just one or the other.

The NAG-1 amount can obtained by adding wild type NAG-1 and H6D protein levels can be obtained by measuring an amount of form-specific antibodies for wild type NAG-1 and H6D proteins.

The amount of the NAG-1 can be measured by performing an assay such as, but not limited to, ELISA, radioimmunoassay, or fluoroimmunoassays. The biological system sampled is preferably one of plasma, urine, cerebrospinal fluids, bile and joint fluids.

The cancer detected can be any that are characterized by increased levels of PSA and NAG-1. Preferably, the cancer is prostate, breast, colon, or pancreatic.

In a specific example of this method, diagnosis was made of a segment of prostate cancer patients who have high NAG-1 and high PSA levels in biological samples as prostate cancer patients with cancer-associated inflammation. NAG-1 levels were measured by sandwich ELISA for plasma samples (54 control and 37 prostate cancer) and each NAG-1 value was compared with corresponding PSA level of each patient (Table 3 and FIG. 8). Detailed information about the plasma samples is described in Example 9. Among the 37 prostate cancer plasma samples, 3 samples (8%) showed extremely high NAG-1 levels (17.7, 3.4 and 2.4 ng/ml) compared to other 34 cancer samples (Table 3, FIG. 8, Panel A). Interestingly, these are the only 3 samples with high PSA levels of 120, 335, and 754 ng/ml compared to the other cancer samples (Table 3, FIG. 8, Panel B). One control sample out of 54 showed 2.3 ng/ml NAG-1 level but the PSA level was 1 ng/ml, the cut-off point for normal value, <4 ng/ml. It was found that the 3 plasma samples obtained from prostate cancer patients had PSA levels≥120 ng/ml.

Mean NAG-1 and PSA values of the 54 control samples were 117.2 pg/ml and 3.5 ng/ml, respectively, and mean NAG-1 and PSA values of the cancer group was 737 pg/ml and 40 ng/ml, respectively. The 3 high NAG-1 (17.7, 3.4 and 2.4 ng/ml) and high PSA (120, 335, and 754 ng/ml) group, which contained >10-fold higher levels than the mean control NAG-1 and PSA levels, 1.17 and 35 ng/ml, respectively, were designated as a cancer-associated inflammatory group. One control subject has 2.3 ng/ml NAG-1 level but is not qualified to belong to the cancer-associated inflammatory group because her/his PSA level is 1 ng/ml, lower than 35 ng/ml (10-fold levels of the mean control PSA level).

This method, which selected 3 out of 91 persons as a patient with the cancer-associated inflammation can also be used to designate a cancer-associated inflammation group in various cancer patients including breast, colon and pancreatic cancer patients. The patient designated as a patient with the cancer-associated inflammation by this method will benefit from treatment with anti-inflammatory molecules including the NAG-1 antibodies. Extremely high NAG-1 levels were reported to be associated with cancer-induced anorexia and weight loss caused by cancer-associated inflammation (16). NAG-1 antibody treatment improved the cancer-induced anorexia and weight loss in a mouse study (16).

The present invention also provides for a method of treating cancer, by administering an effective amount of anti-peptide form-specific antibodies that react with wild type NAG-1 and an H6D polymorphism. Preferably, the anti-peptide form-specific antibodies cross-react with SEQ ID NO: 3 and SEQ ID NO: 5. Cancer-associated inflammation can also be reduced by this treatment. The form-specific antibodies can be administered in combination with other inflammation treatments. The form-specific antibodies can also be administered in combination with other cancer treatments, such as, but not limited to, surgery, chemotherapy, and/or radiotherapy.

In methods of the present invention, the biological sample is generally selected from biological fluids, which contain the NAG-1 proteins and can include plasma, urine, cerebrospinal fluids, bile and joint fluids. Plasma is the preferred sample. In general, ELISAs are the preferred immunoassays employed to assess the amount of NAG-1 proteins. ELISA assays are well known to those skilled in the art. Polyclonal, monoclonal and recombinant antibodies can be used in the assays. Where appropriate other immunoassays, such as radioimmunoassays (RIAs) or fluoroimmunoassays (FIAs) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 and may be adapted to be used the method of the present invention. Most of the techniques used to produce antibodies are widely practiced in the art, and most practitioners are familiar with the standard resource materials, which describe specific conditions and procedures. However, for convenience, the following paragraphs may serve as a guideline.

Antibody production: Antibodies (immunoglobulins) may be either monoclonal or polyclonal and are raised against the immunogen. Such immunogens can be used to produce antibodies by standard antibody production technology well known to those skilled in the art as described generally in Harlow and Lane, Antibodies: A laboratory Manual, Cold Spring Harbor Laboratory, Cold Spring Harbor, N.Y., 1988 and Borrebaeck, Antibody Engineering—A practical Guide, W. H. Freeman and Co., 1992. Antibody fragments may also be prepared from the antibodies and include Fab, F(ab')$_2$, and Fv by methods known to those skilled in the art. For producing recombinant antibody (13-15), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. The methods used with and the utility of the present invention can be shown by the following non-limiting examples and accompanying figures.

The compounds (peptides and antibodies) of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compounds of the present invention can be administered in various ways. It should be noted that they can be administered as the compounds and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compounds of the present invention parenterally, they will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Materials and Methods

Materials

Wild type NAG-1 peptide, CRNGDH (Peptide 1, SEQ ID NO: 1), and H6D peptide, CRNGDD (Peptide 2, SEQ ID NO: 2), and N-terminal peptides of the cleaved NAG-1 and H6D, ARNGDHC (SEQ ID NO: 28) and ARNGDDC (SEQ ID NO: 29), respectively, were obtained from Invitrogen. Other reagents were obtained from Sigma Chemical Co. (St. Louis, Mo.).

Methods

Antibody Production

Wild type NAG-1 peptide, CRNGDH (Peptide 1, SEQ ID NO: 1), and H6D peptide, CRNGDD (Peptide 2, SEQ ID NO: 2), and N-terminal peptides of the cleaved NAG-1 and H6D, ARNGDHC (SEQ ID NO: 28) and ARNGDDC (SEQ ID NO: 29), were conjugated with KLH, BSA or ovalbumin (OVA) via the sulfhydryl side chain of Cys.

Polyclonal antibodies for wild type NAG-1 and H6D proteins were produced at AnaSpec (San Jose, Calif.) by immunization of two rabbits for each peptide antigen. Anti-goat for C-terminal NAG-1 antibody was produced by Cocalico (Reamstown, Pa.).

Monoclonal antibodies for wild type NAG-1 and H6D proteins were produced at Open Biosystems (Huntsville, Ala.) by immunization of 5 mice for each peptide antigen. Hybridomas were produced with the standard procedure routinely used at Open Biosystems.

Purification of IgG Fraction of Antisera

The IgG fraction of antibodies were purified from sera using protein-G affinity chromatography (Pierce Co.). The IgG bound to the protein G column was eluted with 50 mM glycine-HCl buffer, pH 2.5, and immediately neutralized with 0.5 M tris-HCl, pH 7.6. This procedure did not affect the specificity of the antibodies.

Conventional (Direct) and Sandwich ELISA Analyses

Direct ELISA was carried out using peptide conjugated to BSA or OVA. Briefly, 1 µg of peptide-conjugated BSA or ovalbumin (OVA) and free BSA or OVA were coated on a 96-well plate overnight in 1 M sodium bicarbonate, pH 9.6. Non-specific sites were blocked by the addition of 0.2 ml of 10% nonfat dry milk in TBS, pH 7.5, and plates were incubated for 2 hr at room temperature.

Antiserum was diluted 6,000-fold in TBS and added to wells and incubated for 2 hr at room temperature, followed by incubation for 1 hr with various dilutions of goat anti-rabbit IgG-horseradish peroxidase (HRP) secondary antibody. After washing, the color was developed by the addition of 0.2 ml of TMB (3,3',5,5'-tetramethylbenzidine). The reaction was stopped in ~5-10 min by addition of 50 µl of 3 N $H_2SO_4$, and the absorbance at 450 nm was obtained using a microtiter plate reader.

Human wild type NAG-1- or H6D-specific sandwich ELISAs were produced using capture and detection antibodies. Various concentrations of 100 µl NAG-1 standards (50 pg/ml-100 ng/ml recombinant NAG-1, R&D Systems) or plasma samples (25 µl) were captured by form-specific wild type NAG-1 or H6D IgG produced at Detroit R&D (5-20 µg/well) coated on a 96-well plate. After 2 hours incubation with standards or diluted samples at room temperature, the plate was washed and incubated with capture antibodies raised against recombinant cleaved NAG-1 proteins (R&D Systems) (3,000-fold dilution). Levels of the bound detection antibodies were detected by secondary IgG conjugated with HRP. Absorbance was detected at 450 nm after addition of HRP substrate [3,3',5,5' tetramethylbenzidine (TMB) and hydrogen peroxide] (Sigma) and quenching with 3 N $H_2SO_4$ after 10 minutes. For the human NAG-1 sandwich ELISA, various concentrations of 200 µl NAG-1 standard solutions (0.01 pg/ml-1 ng/ml recombinant NAG-1, R&D Systems) or 40-fold diluted plasma samples (5 µl/200 µl) were used.

Statistics

Statistical analysis was carried out using Statview 512 software (Brain Power, Inc., Calabasas, Calif.) and significance between groups was analyzed using one factor anova (Scheffe F-test).

Example 1

Form-Specific Antigen Peptide Design and KLH Conjugation

The approach was to design peptides, CRNGDD (SEQ ID NO: 2) and CRNGDH (SEQ ID NO: 1), which contain N-terminal Cys to allow peptide conjugation with KLH in a specific orientation. By this method, H6 or D6 at the C-terminus of the peptide protruded to the solution and was recognized as an epitope during antibody production. Successful form-specific antibodies produced for NAG-1 and H6D proteins using this strategy were a surprise. CRNGDH (Peptide 1, SEQ ID NO: 1) and CRNGDD (Peptide 2, SEQ ID NO: 2) peptides were obtained from Invitrogen and the peptides were conjugated with KLH, BSA and ovalbumin (OVA) via the sulfhydryl side chain of Cys. The peptides conjugated with BSA or OVA were used for an antibody titer measurement and assessment of specificity.

Example 2

Form-Specific Wild Type NAG-1 and H6D Polyclonal Antibody Production and Characterization of Specificity Polyclonal antibodies for wild type NAG-1 and H6D proteins were produced at AnaSpec by immunization of two rabbits for each peptide antigen. Titers of the NAG-1 and H6D anti-peptide antibodies were measured with 5,000-through 3,500,000-fold diluted pre-immune sera and first bleed sera obtained after the 2nd immunization using ELISA plates coated with NAG-1 or H6D peptide-conjugated BSA.

Whereas pre-immune sera showed almost no cross-reactivity (optical density at 450 nm: 0.01-0.04) with NAG-1 or H6D antigen peptide-conjugated BSA, immune sera showed very high cross-reactivity (optical density at 450 nm: 1.3 and 1.2 for two NAG-1 rabbit sera and 2.2 and 1.3 for two H6D rabbit sera with 5,000-fold dilution). This result showed that antibody titers were exceptionally high, especially considering that the bleed used was only after the 2nd immunization.

The second bleed following the 3rd immunization of each rabbit was obtained. Cross-reactivity of H6D polyclonal antibodies with the H6D peptide-conjugated BSA and BSA (negative control) was tested using a direct ELISA. Whereas BSA showed minimal cross-reactivity (optical density at 450 nm, 0.2) with H6D antibody the H6D peptide-conjugated BSA showed very high cross-reactivity (optical density at 450 nm, 8.5 and 0.7 for two H6D rabbit sera. The ELISA result demonstrated that H6D antibodies recognized the peptide sequence of CRNGDD (SEQ ID NO: 2).

To verify the ELISA result obtained with the H6D peptide-conjugated BSA, an inhibition assay was performed with the peptide-conjugated BSA. Western blot analysis was carried out following SDS-PAGE separation of the BSA (1 µg/lane) conjugated with or without CRNGDD (SEQ ID NO: 2) peptide using the primary antibody (6,000-fold dilution) of H6D antibody of Rabbit #1 (A#1) and goat anti-rabbit IgG-HRP secondary antibody (5,000-fold dilution). The peptide bands were visualized by ECL method. BSA without peptide conjugation was subjected to the same conjugation procedure with cross-linking chemical but without the synthetic peptides. The H6D antibody recognized BSA conjugated with peptides whereas minimal cross-reactivity was seen with BSA.

Specificity of the H6D antibodies was tested by peptide-induced antibody binding inhibition studies. The antibody was incubated without or with CRNGDH (SEQ ID NO: 1) peptides, or with CRNGDD (SEQ ID NO: 2) peptides. Whereas cross-reactivity of the H6D antibodies to the CRNGDD (SEQ ID NO: 2) peptide-conjugated BSA was minimally inhibited by addition of high amount of CRNGDH (SEQ ID NO: 1) peptides (10 µg peptide/µl antiserum), cross-reactivity of the H6D antibody to the CRNGDD (SEQ ID NO: 2) peptide-conjugated BSA was substantially (81%) inhibited by addition of the CRNGDD (SEQ ID NO: 2) peptides (10 µg peptide/µl antiserum). This result demonstrated that H6D antibodies are form-specific.

Specificity of the polyclonal antibodies was further characterized using peptide-conjugated with BSA or OVA. The peptides were conjugated at Open Biosystems. The conjugates were reconstituted to a 2 µg/µl solution with PBS. Proteins (2 µg/lane, the conjugates) were separated by SDS-PAGE and electroblotted to a nitrocellulose membrane. Western blot analyses were carried out using rabbit polyclonal antibodies produced against the CRNGDH (Peptide 1, SEQ ID NO: 1) and CRNGDD (Peptide 2, SEQ ID NO: 2). Recognition of the antibodies to the BSA- and OVA-peptide conjugates was visualized by an HRP/ECL system. Anti-Peptide 1 cross-reacted with BSA- or OVA-Peptide 1 but NOT with BSA- or OVA-Peptide 2 and anti-Peptide 2 cross-reacted with BSA- or OVA-Peptide 2 but NOT with BSA- or OVA-Peptide 1 (FIGS. 1A-1B). This result confirmed specificity of the antibodies. The BSA-Peptides showed monomer, dimer, trimer and even higher polymers because, during peptide conjugation, various peptide-conjugated BSA polymers were produced by the cross-linking chemicals.

Example 3

Wild Type NAG-1- or H6D-Specific Monoclonal Antibody Production

Peptide 1 for the wild type (CRNGDH, SEQ ID NO: 1) and Peptide 2 for H6D (CRNGDD, SEQ ID NO: 2) were conjugated to KLH via sulfhydryl side chain of N-terminal Cys of the peptides. Five mice were immunized at Open Biosystems with each peptide-KLH conjugate for monoclonal antibody production.

(a) Wild Type NAG-1 Antibody:

Cross-reactivities of Mice #1 and #2 bleeds with Peptide 1-conjugated BSA were detected by ELISA (titers of 62,500 and 2,500, respectively). After a final immunization, Mice #1 and #2 were sacrificed and their spleen cells were fused with myeloma cells for hybridoma production.

ELISAs for supernatants (12 from Mouse #1 and 3 from Mouse #2) obtained from NAG-1 (anti-Peptide 1) hybridoma cell culture were carried out with a plate coated with Peptide 1- and Peptide 2-conjugated OVA. Clones with an optical density (OD) at 450 nm higher than 0.4 (background OD) were selected and are shown in Table 1.

Clones 1-2, 1-3 and 2-1 were assumed to be as NAG-1 specific antibodies because after subtraction of background OD, they recognized primarily Peptide-1-OVA conjugate.

TABLE 1

| A. Mouse #1 | | |
|---|---|---|
| CLONE | EH060802K (Peptide 1) OVA | EH060803K (Peptide 2) OVA |
| 1-1 | —[a] | 0.048 |
| 1-2 | 1.187 | 0.132 |
| 1-3 | 0.603 | 0.132 |
| 1-4 | 0.366 | 0.399 |
| 1-5 | 0.991 | 0.521 |
| 1-6 | 0.295 | 0.105 |
| 1-7 | 0.085 | 0.012 |
| 1-8 | 0.040 | — |
| 1-9 | 0.239 | 0.063 |
| 1-10 | 0.078 | 0.054 |
| 1-11 | — | 0.065 |
| 1-12 | — | 0.072 |

| B. Mouse #2 | | |
|---|---|---|
| CLONE | EH060802K (Peptide 1) OVA | EH060802K (Peptide 2) OVA |
| 2-1 | 0.508 | 0.175 |
| 2-2 | 0.050 | — |
| 2-3 | 0.246 | 0.232 |

ELISA carried out with supernatant of hybridomas obtained from mice immunized with Peptide 1-conjuugated KLH.
ELISA was carried out with a microtiter plated coated with OVA conjugated with Peptide 1 or 2.
Net optical densities (ODs) at 450 nm after background OD (0.4) was subtracted are shown.
Clones 1-1, 1-2 and 2-1 are NAG-1 specific antibodies.
[a]lower than background OD.

(b) H6D Antibody:

Mice #3 and #5 were selected after immunization of the mice with Peptide-2-KLH conjugates by ELISA with a plate coated with Peptide 2-conjugated BSA.

Only 3 hybridomas, all of which were obtained from Mouse #5 (2nd mouse used for H6D hybridoma production), showed OD 450 nm values higher than 0.4 when ELISA was carried out with a plate coated with Peptide 1- and Peptide 2-conjugated OVAs (Table 2). Clone 2-1 was assumed to be an H6D specific antibody because after subtraction of background OD, it recognized primarily Peptide-2-OVA conjugates.

TABLE 2

| CLONE | EH060802K (Peptide 1) OVA | EH060802K (Peptide 2) OVA |
|---|---|---|
| 2-1 | 0.016 | 0.552 |
| 2-2 | —[a] | 0.040 |
| 2-3 | — | 0.032 |

ELISA carried out with supernatants of hybridomas obtained from mice immunized with Peptide 2-conjugated KLH.
ELISA was carried out with a microtiter plate coated with OVA conjugated with peptide 1 or 2.
Net optical densities (ODs) at 450 nm agter background OD (0.4) was subtracted are shown.
Clone 2-1 is H6D specific antibodies.
[a]lower than background OD.

Example 4

Human Serum Study by Western Blot Analysis Under Non-Reducing Conditions

Expression of ~40 kDa and total immunoreactive H6D or NAG-1 proteins were studied with 9 coded human serum samples with an inflammatory lung disease, chronic obstructive pulmonary disease (COPD), and with 4 control and 4 lung cancer patients obtained from the University of Michigan.

The serum proteins (1 µl serum/lane) were subjected to Western blot analyses under non-reducing conditions with 2,000-fold diluted H6D or NAG-1 primary antibodies and 5,000-fold diluted secondary antibody/HRP conjugates, and ~40 kDa dimeric and high molecular weight (>120 kDa) H6D and NAG-1 proteins were identified after visualizing bands by ECL method. Intensity of the bands was visualized by autoradiogram and relative density of the 40 kDa and total immunoreactive wild type NAG-1 or H6D proteins were obtained. Differential expression levels of the ~40 kDa and the total immunoreactive H6D or wild type NAG-1 proteins in the human sera were detected among the serum samples: one of the COPD patient sera contained ~4-fold higher level of the 40 kDa wild type NAG-1 species compared with H6D and Serum sample #4 in the lung cancer study had much higher wild type NAG-1 level compared with the H6D level (FIG. 2).

Example 5

Wild Type NAG-1 Sandwich ELISA Production

An human NAG-1 sandwich ELISA was produced using the form-specific wild type NAG-1 IgG produced at Detroit R&D (5-20 µg/well) that has been coated overnight at room temperature in 1 M sodium carbonate, pH 9.6. Various concentrations of NAG-1 standards were captured by 2 hours incubation at room temperature. Absorbance was detected at 450 nm after addition of TMB. Linear regression analysis of the wild type NAG-1 ELISA has an $R^2$ value of 0.99. The sensitivity of the antibodies was at least 50 pg/ml (FIG. 3), which was in the proper for human serum screening. The ELISA result proved that both antibodies produced for RNGDH (SEQ ID NO: 3) (capture antibodies, Detroit R&D) and the monoclonal antibodies for NAG-1 proteins (detection antibodies, R&D Systems) simultaneously bound to the NAG-1 molecule suggesting the epitope of the monoclonal antibodies differs from the epitope of the wild type NAG-1 antibodies. Thus, it is expected that the H6D sandwich ELISA produced for RNGDD (SEQ ID NO: 5) has sensitivity similar to the NAG-1 sandwich ELISA.

Example 6

Quantitation of Wild Type NAG-1 Levels of 9 Human COPD Patient Serum Samples Using NAG-1 Sandwich ELISA Using an ELISA plate coated with the wild type NAG-1 IgG produced with the wild type NAG-1 peptide (RNGDH, SEQ ID NO: 3) at Detroit R&D (capture antibody), NAG-1 levels in serum samples obtained from 9 COPD patients were measured. A standard curve using the wild type NAG-1 protein (FIG. 3) was used to calculate the NAG-1 concentration of each sample (FIG. 4, Panels A and B). ELISA results showed that the wild type NAG-1 levels of the 9 human serum samples were in the range of 100 pg/ml-3 ng/ml, which was slightly higher than the level of the control previously reported to be in a range of 200 pg/ml-1.5 ng/ml by Brown et al. (19).

Example 7

Mouse NAG-1 Anti-Peptide Antibody Production

Mouse NAG-1 has ~65% amino acid identity with human NAG-1. Thus, NAG-1/H6D antibodies produced with the human recombinant protein may not bind or weakly bind to the mouse form. A peptide sequence, HPRDS (SEQ ID NO: 4), was selected for mouse-specific anti-peptide antibody production using a previously published alignment of the NAG-1 sequences of 5 species (9). Because human anti-peptide antibodies were successfully made against RNGDH (SEQ ID NO: 3) and RNGDD (SEQ ID NO: 5), a mouse sequence corresponding to the human sequence, HPRDS (SEQ ID NO: 4), was selected for the mouse NAG-1 antibody production though only 1 amino acid out of 5 was conserved.

Cys was added to the N-terminal of the peptide sequence and the peptide was conjugated to KLH via the SH group of the Cys. Anti-peptide antibodies were produced at AnaSpec by immunization of rabbits with the peptide conjugated to KLH. Western blot analysis was carried out with pooled (male and female) mouse sera (1 µl/lane) obtained from Innovative Research (Novi, Mich.) using 4-16% gradient SDS-PAGE. NAG-1 bands were visualized by an anti-mouse IgG conjugated HRP/ECL system. An ~12 kDa species (cleaved NAG-1 monomer) and other immunoreactive species with high molecular weight were detected (FIG. 5). Goat anti-peptide antibodies were produced by Detroit R&D against the human NAG-1 C-terminal sequence, KTDTGVSLQTYD-DLLA (SEQ ID NO: 31), after conjugation of the peptide to KLH via N-terminally added Cys. The goat C-terminal antibodies cross-reacted with the high molecular weight species in the mouse serum because of the highly conserved mouse sequence, RTDSGVSLQTYDDLVA (SEQ ID NO: 32) (conserved amino acid is in bold type).

This result demonstrated that NAG-1 anti-peptide antibodies are successfully produced for other species against the sequences corresponding to the human sequences, RNGDH (SEQ ID NO: 3) and RNGDD (SEQ ID NO: 5), after the N-terminal Cys is added to the peptide for KLH conjugation. The target sequences identified for various species are shown in bold type in the sequence alignment (FIG. 6, Panel A). The anti-peptide antibodies will cross-react native NAG-1 protein as human wild type NAG-1 and H6D antibodies cross-reacted with the NAG-1 proteins in ELISA because secondary (alpha-helix, beta-sheet and beta-turn) and tertiary (domain and subdomain) structures are generally more conserved than the primary (amino acid) sequence. For example, anti-peptide antibodies for dog NAG-1 proteins can also be produced using CHARDG (SEQ ID NO: 33). Human wild type NAG-1 antibodies against RNGDH (SEQ ID NO: 3) also cross-react with chimpanzee NAG-1 (100% amino acid identity) and mouse NAG-1 antibodies against HPRDS (SEQ ID NO: 4) cross-react with rat NAG-1 (100% amino acid identity) in Western blot analysis and ELISA. The amino acid sequences of TGF-beta subfamily proteins corresponding to the human NAG-1 sequence, RNGDH (SEQ ID NO: 3), suitable for antibody production after addition of N-terminal Cys is shown in FIG. 6, Panel B (underlined and in bold type).

Example 8

Production of Cleavage-Specific NAG-1 Antibodies and Antibody Specific for Pro-NAG-1

Mature 112 amino acid-length proteins secreted to blood are formed by furin digestion of the pro-NAG-1 between RRAR (SEQ ID NO: 34) and ARNGDHC (Peptide 1, SEQ ID NO: 28) or ARNGDDC (Peptide 2, SEQ ID NO: 29) (8). Anti-peptide antibodies against a sequence of ARNGDHC (cleaved) (wild type NAG-1) were produced at AnaSpec by immunization of rabbits with the ARNGDHC (SEQ ID NO: 28) peptide conjugated to KLH via the C-terminal Cys. The His or Asp at $6^{th}$ position was located near the Cys and the sulfhydryl group of the Cys was utilized to conjugate the peptide to KLH. All polyclonal antibodies produced by immunizing four rabbits with Peptide 1-conjugated KLH recognized both ARNGDHC (Peptide 1, SEQ ID NO: 28)- and ARNGDDC (Peptide 2, SEQ ID NO: 29)-conjugated BSA in Western blot analyses (FIGS. 7A-7B). Thus, the antibodies do not distinguish the wild type NAG-1 protein from H6D. This result demonstrated that the orientation of the target sequence toward solution during antibody production is an important factor in deciding the specificity of the antibody. Because the N-terminus of the ARNGDHC (Peptide 1, SEQ ID NO: 28) contains the $NH_3^+$ group of the peptide, which is exposed to solution during antibody production, the antibody preferably binds to the mature, cleaved NAG-1 protein. Improvement of specificity of the cleavage-specific antibodies can be achieved by eliminating antibodies, which bind to RARNGDHC (SEQ ID NO: 35) or RARNGDDC (SEQ ID NO: 36) using RARNGDHC (SEQ ID NO: 35) or RARNGDDC (SEQ ID NO: 36) peptide affinity chromatography.

The flow-through fraction will contain cleavage-specific NAG-1 antibodies. Pro-NAG-1 antibodies can be produced by immunization of an animal with RARNGDHC (SEQ ID NO: 35) or RARNGDDC (SEQ ID NO: 36) conjugated to KLH.

Cleavage-specific or pro-NAG-1 can also be produced for other TGF-beta subfamily expressed in various species after selecting a sequence corresponding to the human peptide sequence, ARNGDHC (SEQ ID NO: 28), as shown in FIG. 6, Panels C and D. The sequences selected for cleavage-specific antibody production are underlined and in bold type. Addition of Arg to the N-terminus of the selected sequences will produce antigen sequences for pro-NAG-1.

Example 9

NAG-1 Levels in Plasma Samples Obtained from Control and Prostate Cancer Patients NAG-1 levels were measured by sandwich ELISA for plasma samples (54 control and 37 prostate cancer) obtained from Henry Ford Hospital, MI. Two control samples without available PSA values were not included for this study. Detailed criteria used to assign each sample to control and prostate cancer has been previously published (17). ELISA was carried out as described in Methods.

Among the 37 prostate cancer plasma samples, three samples showed extremely high NAG-1 levels, 17.7 ng/ml (Plasma No. Cancer 22), 3.4 ng/ml (Plasma No. Cancer 21) and 2.4 ng/ml (Plasma No. Cancer 30), compared to other prostate cancer plasma samples, which showed lower than 0.4 ng/ml (Table 3, FIG. 8, Panel A). Interestingly, these are the only three samples with high PSA levels of 120 ng/ml (Plasma No. Cancer 22), 335 ng/ml (Plasma No. Cancer 21) and 754 ng/ml (Plasma No. Cancer 30) compared to other cancer samples, which showed lower than 30 ng/ml (Table 3, FIG. 8, Panel B).

TABLE 3

Plasma NAG-1 and PSA levels from controls and prostate cancer patients.

| | Control | | | Prostate Cancer | |
|---|---|---|---|---|---|
| Sample No. | NAG-1 (pg/ml) | PSA (ng/ml) | Sample No. | NAG-1 (pg/ml) | PSA (ng/ml) |
| 1 | 19 | 1.7 | 1 | 13 | 1.2 |
| 2 | 80 | 0.7 | 2 | 185 | 4.4 |
| 3 | N/I (68) | N/A | 3 | 391 | 4.2 |
| 4 | 136 | 6.6 | 4 | 41 | 4.7 |
| 5 | 52 | 6.2 | 5 | 41 | 5.5 |
| 6 | 52 | 19.9 | 6 | 47 | 9.8 |
| 7 | 120 | 7.9 | 7 | 31 | 4.7 |
| 8 | 49 | 0.2 | 8 | 45 | 4.7 |
| 9 | N/I (16) | N/A | 9 | 70 | 4.5 |
| 10 | 71 | 1 | 10 | 27 | 4.8 |
| 11 | 15 | 0.2 | 11 | 140 | 4.9 |
| 12 | 47 | 0.5 | 12 | 34 | 26.4 |
| 13 | 57 | 10.9 | 13 | 121 | 2.1 |
| 14 | 13 | 7.8 | 14 | 47 | 30.3 |
| 15 | 132 | 4.2 | 15 | 151 | 4.5 |
| 16 | 12 | 3 | 16 | 383 | 2.3 |
| 17 | 22 | 1.4 | 17 | 383 | 17.1 |
| 18 | 202 | 1.1 | 18 | 320 | 17.1 |
| 19 | 152 | 4.4 | 19 | 113 | 4.8 |
| 20 | 43 | 0.9 | 20 | 13 | 11.7 |
| 21 | 2293 | 1 | 21 | 3413 | 335.4 |
| 22 | 92 | 5.7 | 22 | 17716 | 120.6 |
| 23 | 93 | 7.8 | 23 | 587 | 9 |
| 24 | 145 | 7 | 24 | 253 | 4.7 |
| 25 | 4 | 0.6 | 25 | 33 | 7.4 |
| 26 | 2 | 0.3 | 26 | 3 | 2.5 |
| 27 | 409 | 0.3 | 27 | 25 | 4.3 |
| 28 | 0.3 | 0.3 | 28 | 6 | 5.2 |
| 29 | 3 | 6.1 | 29 | 116 | 6 |
| 30 | 3 | 1.1 | 30 | 2400 | 754.9 |
| 31 | 31 | 3.1 | 31 | 10 | 29.3 |
| 32 | 293 | 0.5 | 32 | 29 | 6.8 |
| 33 | 11 | 4.8 | 33 | 17 | 4.4 |
| 34 | 73 | 0.4 | 34 | 27 | 5 |
| 35 | 304 | 1.2 | 35 | 6 | 4.3 |
| 36 | 87 | 0.7 | 36 | 20 | 5.9 |
| 37 | 316 | 6.2 | 37 | 10 | 6.1 |
| 38 | 427 | 1.6 | Total | 27267 | 1481.5 |
| 39 | 3 | 1.2 | Mean | 737 | 40 |
| 40 | 11 | 0.3 | | n = 36 | n = 36 |
| 41 | 1 | 1.1 | | | |
| 42 | 8 | 0.5 | | | |

TABLE 3-continued

Plasma NAG-1 and PSA levels from controls and prostate cancer patients.

| | Control | | | Prostate Cancer | |
|---|---|---|---|---|---|
| Sample No. | NAG-1 (pg/ml) | PSA (ng/ml) | Sample No. | NAG-1 (pg/ml) | PSA (ng/ml) |
| 43 | 5 | 6 | | | |
| 44 | 3 | 0.7 | | | |
| 45 | 6 | 0.6 | | | |
| 46 | 4 | 0.5 | | | |
| 47 | 120 | 1.3 | | | |
| 48 | 20 | 4.3 | | | |
| 49 | 77 | 0.9 | | | |
| 50 | 13 | 0.5 | | | |
| 51 | 15 | 1 | | | |
| 52 | 6 | 0.3 | | | |
| 53 | 19 | 4.9 | | | |
| 54 | 152 | 15.4 | | | |
| 55 | 3 | 5.5 | | | |
| 56 | 3 | 18.9 | | | |
| Total | 6329.3 | 191.2 | | | |
| Mean | 117.2 | 3.5 | | | |
| | n for study = 54 | n for study = 54 | | | |

N/A, Not available, N/I, Not included for this study because a corresponding PSA level is not available.

Three out of 37 (~8%) prostate cancer patients in this study group had plasma PSA levels over 30-fold higher than the cut-off point for control group (4 ng/ml). Plasma No. Control 21 showed 2.3 ng/ml NAG-1 level with 1 ng/ml PSA level. In other words, all three prostate cancer plasma samples, which had PSA levels≥120 ng/ml (over 30-fold higher than cut-off point for control, 4 ng/ml) had extremely high NAG-1 levels. A recent study revealed that, in prostate, colon, pancreas and breast cancers, NAG-1 level increases by 10-100 fold from a mean value, which is associated with cancer-induced anorexia and weight loss (16).

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Martinez J M, Sali T, Okazaki R, Anna C, Hollingshead M, Hose C, Monks A, Walker N J, Baek S J, Eling T E 2006 Drug-induced expression of nonsteroidal anti-inflammatory drug-activated gene/macrophage inhibitory cytokine-1/prostate-derived factor, a putative tumor suppressor, inhibits tumor growth. J Pharmacol Exp Ther 318, 899-906
2. Baek S J, Kim K S, Nixon J B, Wilson L C, Eling T E 2001 Cyclooxygenase inhibitors regulate the expression of a TGF-beta superfamily member that has proapoptotic and antitumorigenic activities. Mol Pharmacol 59, 901-908
3. Eling, T E, Baek S J, Shim, M, Lee, C H 2006 NSAID activated gene (NAG-1), a modulator of tumorigenesis. J. Biochem. Mol. Biol. 39:649-655 and references therein.
4. Brown D A, Bauskin A R, Fairlie W D, Smith M D, Liu T, Xu N, Breit S N 2002 Antibody-based approach to high-volume genotyping for MIC-1 polymorphism. Biotechniques 33:118-120, 122, 124
5. Welsh, J B, Sapinoso, L M, Kern, S G, Brown, D A, Liu, T, Bauskin, A R, Ward, R L, Hawkins, N J, Quinn, D I, Russell, P J, Sutherland, R L, Breit, S N, Moskaluk, C A, Frierson, Jr., H F, Hampton, G M 2003 Large-scale delineation of secreted protein biomarkers overexpressed in cancer tissue and serum. PNAS 100, 3410-3415
6. Selander, K S, Brown, D A, Sequeiros, G B, Hunter, M, Desmond, R, Parpala, T, Risteli, J, Breit, S N, Jukkola-Vuorinen, A 2007 Serum macrophage inhibitory cytokine-1 concentrations correlate with the presence of prostate cancer bone metastases Cancer Epidemiol Biomarkers Prev 16, 532-537
7. Brown, D A, Stephan, C, Ward, R L, Law, M, Hunter, M, Bauskin, A R, Amin, J, Jung, K, Diamandis, E P, Hampton, G M, Russell, P J, Giles, G G, Breit, S N 2006 Measurement of serum levels of macrophage inhibitory cytokine 1 combined with prostate-specific antigen improves prostate cancer diagnosis. Clin Cancer Res 12, 89-96
8. Fairlie W D, Moore A G, Bauskin A R, Russell P K, Zhang H P, Breit S N 1999 MIC-1 is a novel TGF-beta superfamily cytokine associated with macrophage activation. J Leukoc Biol 65, 2-5
9. Lindmark F, Zheng S L, Wiklund F, Bensen J, Batter K A, Chang B, Hedelin M, Clark J, Stattin P, Meyers D A, Adami H O, Isaacs W, Gronberg H, Xu J 2004 H6D polymorphism in macrophage-inhibitory cytokine-1 gene associated with prostate cancer. J Natl Cancer Inst 96, 1248-1254
10. Hayes, V M, Severi, G, Southey, M C, Padilla, E J D, English, D R, Hopper, J L, Giles, G G, Sutherland, R L 2006 Macrophage inhibitory cytokine-1 H6D polymorphism, prostate cancer risk, and survival. Cancer Epidemiol Biomarkers Prev 15, 1223-1225
11. Fairlie W D, Russell P K, Wu W M, Moore A G, Zhang H P, Brown P K, Bauskin A R, Breit S N 2001 Epitope mapping of the transforming growth factor-beta superfamily protein, macrophage inhibitory cytokine-1 (MIC-1): identification of at least five distinct epitope specificities. Biochemistry 40, 65-73
12. Yamaguchi, K., Whitlock, N C, Liggett, J L, Legendre, A M, Michael M. Fry, M M and Baek, S J 2008 Molecular characterisation of canine nonsteroidal anti-inflammatory drug-activated gene (NAG-1) Vet J 175, 89-95.
13. Huston et al., 1991 "Protein Engineering of Single-Chain Fv Analogs And Fusion Proteins" in Methods in Enzymology (J J Langone, ed.; Academic Press, New York, N.Y.) 203, 46-88.
14. Johnson and Bird, 1991, "Construction of Single-Chain Fvb Derivatives of Monoclonal Antibodies and Their Production in *Escherichia coli* in Methods in Enzymology (J J Langone, ed.; Academic Press, New York, N.Y.) 203, 88-89.
15. Mernaugh and Menaugh, 1995, "An Overview of Phage-Displayed Recombinant Antibodies" in Molecular Methods in Plant Pathology (R P Singh and U S Singh, eds.; CRC Press Inc., Boca Raton, Fla.) pp. 359-365.
16. Johnen H, Lin S, Kuffner T, Brown D A, Tsai V W, Bauskin A R, Wu L, Pankhurst G, Jiang L, Junankar S, Hunter M, Fairlie W D, Lee N J, Enriquez R F, Baldock P A, Corey E, Apple F S, Murakami M M, Lin E J, Wang C, During M J, Sainsbury A, Herzog H, Breit S N 2007 Tumor-induced anorexia and weight loss are mediated by the TGF-beta superfamily cytokine MIC-1. Nat Med 200713, 1333-40.
17. Neslund-Dudas, C, Bock, C H, Monaghan, K, Nock, N L, Yang, J J, Rundle, A, Tang, D, Rybicki, B A 2007 SRD5A2 and HSD3B2 polymorphisms are associated with prostate cancer risk and aggressiveness. Prostate 67, 1654-1663

What is claimed is:

1. A method of producing form-specific anti-peptide antibodies for a wild type protein and its one amino acid mutated protein using peptide antigens, including the steps of:
   obtaining the protein sequences human wild type NAG-1 and human H6D;
   aligning the human NAG-1 protein sequence with the human H6D sequence;
   verifying that the $2^{nd}$ and $3^{rd}$ cysteines of the human NAG-1 protein sequence correspond to the $2^{nd}$ and $3^{rd}$ cysteines of the human H6D sequence;
   selecting from the NAG-1 protein sequence a first antigen peptide with 5-9 residues, or extended to the next downstream residue of a sequence consisting of SEQ ID NO: 30, which C-terminally ends with an amino acid sequence consisting of SEQ ID NO: 3 or SEQ ID NO: 28 of the human NAG-1 protein;
   selecting from the human H6D protein sequence a second antigen peptide with 5-9 residues, or extended to the next downstream residue of a sequence consisting of SEQ ID NO: 30, which C-terminally ends with an amino acid sequence aligned with a peptide sequence consisting of SEQ ID NO: 3 or SEQ ID NO: 28 of the human wild type NAG-1 protein, the second antigen peptide consisting of SEQ ID NO: 5 or SEQ ID NO: 29;
   synthesizing a first antigen peptide consisting of SEQ ID NO: 3 or SEQ ID NO: 28, and a second antigen peptide consisting of SEQ ID NO: 5 or SEQ ID NO: 29;
   conjugating the first and the second antigen peptides to a carrier protein;
   generating a first antigen peptide-carrier conjugate and a second peptide-carrier conjugate; and
   immunizing an animal against the first or second antigen peptide-carrier conjugate to produce antibodies to, respectively, the first or the second antigen peptides.

2. The method of claim 1, wherein the first antigen peptide consists of SEQ ID NO: 3 and the second antigen peptide consists of SEQ ID NO: 5, and the conjugating step includes the steps of
   adding an N-terminal Cys to the first and the second antigen peptides;
   producing an N-terminal Cys-containing first antigen peptide consisting of SEQ ID NO: 1 and a second N-terminal Cys-containing antigen peptide consisting of SEQ ID NO: 2; and
   conjugating the peptides SEQ ID NO: 1 and SEQ ID NO: 2 to a carrier protein via the N-terminal Cys.

3. A method of producing anti-peptide antibodies for a human or non-human TGF-beta subfamily protein including the steps of:
   obtaining the protein sequence of a human wild type NAG-1 or a human H6D;
   obtaining a protein sequence of a human or non-human TGF-beta subfamily protein;
   aligning the human wild type NAG-1 protein sequence or the human H6D protein sequence with the human or non-human TGF-beta subfamily protein sequence;
   verifying that the $2^{nd}$ and $3^{rd}$ cysteines of the human wild type NAG-1 or the human H6D protein sequence correspond to the $2^{nd}$ and $3^{rd}$ cysteines of the human or non-human TGF-beta subfamily protein sequence;
   selecting from the human or non-human TGF-beta subfamily protein sequence an antigen peptide with 5-9 residues, or extended to the next downstream residue of a sequence consisting of SEQ ID NO: 30, which C-terminally ends with an amino acid sequence aligned with a peptide sequence consisting of SEQ ID NO: 3 or SEQ ID NO: 28 of the human wild type NAG-1 protein, or SEQ ID NO: 5 or SEQ ID NO: 29 of the human H6D protein;
   synthesizing the selected antigen peptide;
   conjugating the selected antigen peptide to a carrier protein;
   generating an antigen peptide-carrier conjugate; and
   immunizing the animal against the antigen peptide-carrier conjugate to produce antibodies to said antigen peptide.

4. The method of claim 1, wherein antibodies are produced against a first antigen peptide consisting of SEQ ID NO: 28, or a second antigen peptide consisting of SEQ ID NO: 29, further including the step of purifying the antibodies by eliminating any antibodies that cross-react with Arg-containing N-terminal peptides of cleaved proteins.

5. The method of claim 1 or claim 3, further including the step of confirming the presence of antibodies by taking a sample from the patient and performing an assay chosen from the group consisting of ELISA, radioimmunoassay, and fluoroimmunoassays.

6. The method of claim 3, wherein the human or non-human TGF-beta subfamily protein is mouse or rat NAG-1, and the conjugating step includes the steps of
- adding an N-terminal Cys to the first antigen peptide;
- producing a N-terminal Cys-containing first antigen peptide consisting of SEQ ID NO: 17; and
- conjugating the peptide consisting of SEQ ID NO: 17 to a carrier protein via the N-terminal Cys.

* * * * *

SEQUENCE LISTING

<160> NUMBER OF SEQ ID NOS: 36

<210> SEQ ID NO 1
<211> LENGTH: 6
<212> TYPE: PRT
<213> ORGANISM: Artificial sequence
<220> FEATURE:
<223> OTHER INFORMATION: Peptide for conjugation.  The peptide is
      synthesized.

<400> SEQUENCE: 1

Cys Arg Asn Gly Asp His
1               5

<210> SEQ ID NO 2
<211> LENGTH: 6
<212> TYPE: PRT
<213> ORGANISM: Artificial sequence
<220> FEATURE:
<223> OTHER INFORMATION: Peptide for conjugation. The peptide is
      synthesized.

<400> SEQUENCE: 2

Cys Arg Asn Gly Asp Asp
1               5

<210> SEQ ID NO 3
<211> LENGTH: 5
<212> TYPE: PRT
<213> ORGANISM: Artificial sequence
<220> FEATURE:
<223> OTHER INFORMATION: Equivalent to the N-terminus of cleaved NAG-1
      in Homo sapiens or Pan troglodytes.

<400> SEQUENCE: 3

Arg Asn Gly Asp His
1               5

<210> SEQ ID NO 4
<211> LENGTH: 5
<212> TYPE: PRT
<213> ORGANISM: Artificial sequence
<220> FEATURE:
<223> OTHER INFORMATION: Equivalent to the N-terminus of cleaved NAG-1
      in Mus musculus or Rattus norvegicus.

<400> SEQUENCE: 4

His Pro Arg Asp Ser
1               5

<210> SEQ ID NO 5
<211> LENGTH: 5
<212> TYPE: PRT
<213> ORGANISM: Artificial sequence
<220> FEATURE:
<223> OTHER INFORMATION: Equivalent to the N-terminus of cleaved NAG-1
      in Homo sapiens.

<400> SEQUENCE: 5

Arg Asn Gly Asp Asp
1               5

<210> SEQ ID NO 6
<211> LENGTH: 60
<212> TYPE: PRT
<213> ORGANISM: Homo sapiens

<400> SEQUENCE: 6

Leu Ala Glu Ser Ser Ala Arg Pro Gln Leu Glu Leu His Leu Arg
1               5                  10                  15

Pro Gln Ala Ala Arg Gly Arg Arg Ala Arg Ala Arg Asn Gly Asp
            20                  25                  30

Asp Cys Pro Leu Gly Pro Gly Arg Cys Cys Arg Leu His Thr Val Arg
            35                  40                  45

Ala Ser Leu Glu Asp Leu Gly Trp Ala Asp Trp Val
    50                  55                  60

<210> SEQ ID NO 7
<211> LENGTH: 60
<212> TYPE: PRT
<213> ORGANISM: Homo sapiens

<400> SEQUENCE: 7

Leu Ala Glu Ser Ser Ala Arg Pro Gln Leu Glu Leu His Leu Arg
1               5                  10                  15

Pro Gln Ala Ala Arg Gly Arg Arg Ala Arg Ala Arg Asn Gly Asp
            20                  25                  30

His Cys Pro Leu Gly Pro Gly Arg Cys Cys Arg Leu His Thr Val Arg
            35                  40                  45

Ala Ser Leu Glu Asp Leu Gly Trp Ala Asp Trp Val
    50                  55                  60

<210> SEQ ID NO 8
<211> LENGTH: 60
<212> TYPE: PRT
<213> ORGANISM: Pan troglodytes

<400> SEQUENCE: 8

Leu Ala Glu Ser Ser Ala Arg Pro Gln Leu Glu Leu His Leu Arg
1               5                  10                  15

Ser Arg Ala Ala Arg Gly Leu Arg Ala Arg Ala Arg Asn Gly Asp
            20                  25                  30

His Cys Pro Leu Gly Pro Gly Arg Cys Cys Arg Leu His Thr Val Arg
            35                  40                  45

Ala Ser Leu Glu Asp Leu Gly Trp Ser Asp Trp Val
    50                  55                  60

<210> SEQ ID NO 9
<211> LENGTH: 57
<212> TYPE: PRT
<213> ORGANISM: Mus musculus

<400> SEQUENCE: 9

Leu Pro Ser Gly Gly Ala Gln Leu Glu Leu Arg Leu Arg Val Ala Ala
1               5                  10                  15

Gly Arg Gly Arg Arg Ser Ala His Ala His Pro Arg Asp Ser Cys Pro
            20                  25                  30

Leu Gly Pro Gly Arg Cys Cys His Leu Glu Thr Val Gln Ala Thr Leu
            35                  40                  45

Glu Asp Leu Gly Trp Ser Asp Trp Val
    50                  55

<210> SEQ ID NO 10
<211> LENGTH: 57
<212> TYPE: PRT
<213> ORGANISM: Rattus norvegicus

```
<400> SEQUENCE: 10

Leu Pro Ser Gly Gly Ala Arg Leu Glu Leu His Leu Arg Ser Ala Ala
1               5                   10                  15

Gly Arg Gly Arg Arg Ser Ala His Leu His Pro Arg Asp Ser Cys Pro
                20                  25                  30

Leu Gly Pro Gly Arg Cys Cys His Leu Glu Thr Val Gln Ala Thr Leu
            35                  40                  45

Glu Asp Leu Gly Trp Ser Asp Trp Val
50                  55

<210> SEQ ID NO 11
<211> LENGTH: 58
<212> TYPE: PRT
<213> ORGANISM: Canis familiaris

<400> SEQUENCE: 11

Ala Leu Pro Ser Ala Arg Pro Gln Leu Glu Leu His Trp Arg Pro Arg
1               5                   10                  15

Ala Ala Arg Gly Arg Arg Asn Ala Ala His Ala Arg Asp Gly Cys
                20                  25                  30

Pro Leu Gly Glu Gly Arg Cys Cys Arg Leu Gln Ser Leu Arg Ala Ser
            35                  40                  45

Leu Gln Asp Leu Gly Trp Ala Asn Trp Val
50                  55

<210> SEQ ID NO 12
<211> LENGTH: 59
<212> TYPE: PRT
<213> ORGANISM: Homo sapiens

<400> SEQUENCE: 12

Glu Leu His Leu Arg Pro Gln Ala Ala Arg Gly Arg Arg Arg Ala Arg
1               5                   10                  15

Ala Arg Asn Gly Asp His Cys Pro Leu Gly Pro Gly Arg Cys Cys Arg
                20                  25                  30

Leu His Thr Val Arg Ala Ser Leu Glu Asp Leu Gly Trp Ala Asp Trp
            35                  40                  45

Val Leu Ser Pro Arg Glu Val Gln Val Thr Met
50                  55

<210> SEQ ID NO 13
<211> LENGTH: 59
<212> TYPE: PRT
<213> ORGANISM: Homo sapiens

<400> SEQUENCE: 13

Thr Pro Leu Glu Arg Ala Gln His Leu Gln Ser Ser Arg His Arg Arg
1               5                   10                  15

Ala Leu Asp Thr Asn Tyr Cys Phe Ser Ser Thr Glu Lys Asn Cys Cys
                20                  25                  30

Val Arg Gln Leu Tyr Ile Asp Phe Arg Lys Asp Leu Gly Trp Lys Trp
            35                  40                  45

Ile His Glu Pro Lys Gly Tyr His Ala Asn Phe
50                  55

<210> SEQ ID NO 14
<211> LENGTH: 59
<212> TYPE: PRT
<213> ORGANISM: Homo sapiens
```

-continued

<400> SEQUENCE: 14

Pro Ser Tyr Arg Leu Glu Ser Gln Gln Thr Asn Arg Arg Lys Lys Arg
1               5                   10                  15

Ala Leu Asp Ala Ala Tyr Cys Phe Arg Asn Val Gln Asp Asn Cys Cys
                20                  25                  30

Leu Arg Pro Leu Tyr Ile Asp Phe Lys Arg Asp Leu Gly Trp Lys Trp
            35                  40                  45

Ile His Glu Pro Lys Gly Tyr Asn Ala Asn Phe
    50                  55

<210> SEQ ID NO 15
<211> LENGTH: 59
<212> TYPE: PRT
<213> ORGANISM: Homo sapiens

<400> SEQUENCE: 15

Pro His Arg Leu Asp Asn Pro Gly Gln Gly Gly Gln Lys Lys Arg
1               5                   10                  15

Ala Leu Asp Thr Asn Tyr Cys Phe Arg Asn Leu Glu Glu Asn Cys Cys
                20                  25                  30

Val Arg Pro Leu Tyr Ile Asp Phe Arg Gln Asp Leu Gly Trp Lys Trp
            35                  40                  45

Val His Glu Pro Lys Gly Tyr Tyr Ala Asn Phe
    50                  55

<210> SEQ ID NO 16
<211> LENGTH: 60
<212> TYPE: PRT
<213> ORGANISM: Xenopus laevis

<400> SEQUENCE: 16

Met Pro Ala Glu Arg Ile Asp Thr Val Thr Ser Ser Arg Lys Lys Arg
1               5                   10                  15

Gly Val Gly Gln Glu Tyr Cys Phe Gly Asn Asn Gly Pro Asn Cys Cys
                20                  25                  30

Val Lys Pro Leu Tyr Ile Asn Phe Arg Lys Asp Leu Gly Trp Lys Trp
            35                  40                  45

Ile His Glu Pro Lys Gly Tyr Glu Ala Asn Tyr Cys
    50                  55                  60

<210> SEQ ID NO 17
<211> LENGTH: 6
<212> TYPE: PRT
<213> ORGANISM: Artificial Sequence
<220> FEATURE:
<223> OTHER INFORMATION: Peptide for conjugation.  The peptide is
      synthesized.

<400> SEQUENCE: 17

Cys His Pro Arg Asp Ser
1               5

<210> SEQ ID NO 18
<211> LENGTH: 10
<212> TYPE: PRT
<213> ORGANISM: Artificial Sequence
<220> FEATURE:
<223> OTHER INFORMATION: Peptide for conjugation.  The peptide is
      synthesized.

```
<400> SEQUENCE: 18

Cys Ser Ala His Ala His Pro Arg Asp Ser
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Peptide for conjugation.  The peptide is
      synthesized.

<400> SEQUENCE: 19

Cys Ala His Ala His Pro Arg Asp Ser
1               5

<210> SEQ ID NO 20
<211> LENGTH: 8
<212> TYPE: PRT
<213> ORGANISM: Artificial Sequence
<220> FEATURE:
<223> OTHER INFORMATION: Peptide for conjugation.  The peptide is
      synthesized.

<400> SEQUENCE: 20

Cys His Ala His Pro Arg Asp Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Peptide for conjugation.  The peptide is
      synthesized.

<400> SEQUENCE: 21

Cys Ala His Pro Arg Asp Ser
1               5

<210> SEQ ID NO 22
<211> LENGTH: 10
<212> TYPE: PRT
<213> ORGANISM: Artificial Sequence
<220> FEATURE:
<223> OTHER INFORMATION: Peptide for conjugation.  The peptide is
      synthesized.

<400> SEQUENCE: 22

Cys Asn Ala His Ala His Ala Arg Asp Gly
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Peptide for conjugation.  The peptide is
      synthesized.

<400> SEQUENCE: 23

Cys Ala His Ala His Ala Arg Asp Gly
1               5
```

```
<210> SEQ ID NO 24
<211> LENGTH: 8
<212> TYPE: PRT
<213> ORGANISM: Artificial Sequence
<220> FEATURE:
<223> OTHER INFORMATION: Peptide for conjugation.  The peptide is
      synthesized.

<400> SEQUENCE: 24

Cys His Ala His Ala Arg Asp Gly
1               5

<210> SEQ ID NO 25
<211> LENGTH: 7
<212> TYPE: PRT
<213> ORGANISM: Artificial Sequence
<220> FEATURE:
<223> OTHER INFORMATION: Peptide for conjugation.  The peptide is
      synthesized.

<400> SEQUENCE: 25

Cys Ala His Ala Arg Asp Gly
1               5

<210> SEQ ID NO 26
<211> LENGTH: 4
<212> TYPE: PRT
<213> ORGANISM: Artificial Sequence
<220> FEATURE:
<223> OTHER INFORMATION: Recognition sequence for furin digestion
<220> FEATURE:
<221> NAME/KEY: misc_feature
<222> LOCATION: (2)..(3)
<223> OTHER INFORMATION: Xaa can be any naturally occurring amino acid

<400> SEQUENCE: 26

Arg Xaa Xaa Arg
1

<210> SEQ ID NO 27
<211> LENGTH: 12
<212> TYPE: PRT
<213> ORGANISM: Artificial Sequence
<220> FEATURE:
<223> OTHER INFORMATION: Equivalent to the N-terminus of cleaved NAG-1
      in Canis familiaris

<400> SEQUENCE: 27

Gly Arg Arg Asn Ala His Ala His Ala Arg Asp Gly
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Equivalent to the N-terminus of cleaved NAG-1
      in Homo sapiens or Pan troglodytes

<400> SEQUENCE: 28

Ala Arg Asn Gly Asp His Cys
1               5

<210> SEQ ID NO 29
<211> LENGTH: 7
<212> TYPE: PRT
<213> ORGANISM: Artificial Sequence
```

```
<220> FEATURE:
<223> OTHER INFORMATION: Equivalent to the N-terminus of cleaved NAG-1
      in Homo sapiens

<400> SEQUENCE: 29

Ala Arg Asn Gly Asp Asp Cys
1               5

<210> SEQ ID NO 30
<211> LENGTH: 4
<212> TYPE: PRT
<213> ORGANISM: Artificial Sequence
<220> FEATURE:
<223> OTHER INFORMATION: Recognition sequence for furin digestion
<220> FEATURE:
<221> NAME/KEY: misc_feature
<222> LOCATION: (2)..(3)
<223> OTHER INFORMATION: Xaa can be any naturally occurring amino acid

<400> SEQUENCE: 30

Arg Xaa Xaa Arg
1

<210> SEQ ID NO 31
<211> LENGTH: 16
<212> TYPE: PRT
<213> ORGANISM: Artificial Sequence
<220> FEATURE:
<223> OTHER INFORMATION: Equivalent to the C-terminus of cleaved NAG-1
      in Homo sapiens or Pan troglodytes

<400> SEQUENCE: 31

Lys Thr Asp Thr Gly Val Ser Leu Gln Thr Tyr Asp Asp Leu Leu Ala
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Equivalent to the C-terminus of cleaved NAG-1
      in Mus musculus or Rattus norvegicus

<400> SEQUENCE: 32

Arg Thr Asp Ser Gly Val Ser Leu Gln Thr Tyr Asp Asp Leu Val Ala
1               5                   10                  15

<210> SEQ ID NO 33
<211> LENGTH: 6
<212> TYPE: PRT
<213> ORGANISM: Artificial Sequence
<220> FEATURE:
<223> OTHER INFORMATION: Peptide for conjugation.  The peptide is
      synthesized.

<400> SEQUENCE: 33

Cys His Ala Arg Asp Gly
1               5

<210> SEQ ID NO 34
<211> LENGTH: 4
<212> TYPE: PRT
<213> ORGANISM: Homo sapiens

<400> SEQUENCE: 34

Arg Arg Ala Arg
1
```

```
<210> SEQ ID NO 35
<211> LENGTH: 8
<212> TYPE: PRT
<213> ORGANISM: Artificial Sequence
<220> FEATURE:
<223> OTHER INFORMATION: Equivalent to the N-terminus of cleaved NAG-1
      in Homo sapiens

<400> SEQUENCE: 35

Arg Ala Arg Asn Gly Asp His Cys
1               5

<210> SEQ ID NO 36
<211> LENGTH: 8
<212> TYPE: PRT
<213> ORGANISM: Artificial Sequence
<220> FEATURE:
<223> OTHER INFORMATION: Equivalent to the N-terminus of cleaved NAG-1
      in Homo sapiens

<400> SEQUENCE: 36

Arg Ala Arg Asn Gly Asp Asp Cys
1               5
```